US007074554B2

(12) United States Patent
Ikezu et al.

(10) Patent No.: US 7,074,554 B2
(45) Date of Patent: Jul. 11, 2006

(54) ANTIBODIES SPECIFIC FOR NEBR1 AND METHODS OF USE THEREOF

(75) Inventors: Tsuneya Ikezu, Omaha, NE (US); Gary Leisman, Omaha, NE (US); Kimberly A. Carlson, Omaha, NE (US); Howard E. Gendelman, Omaha, NE (US)

(73) Assignee: The Board of Regents of the University of Nebraska, Omaha, NE (US)

( * ) Notice: Subject to any disclaimer, the term of this patent is extended or adjusted under 35 U.S.C. 154(b) by 167 days.

(21) Appl. No.: 10/732,706

(22) Filed: Dec. 10, 2003

(65) Prior Publication Data

US 2005/0130128 A1    Jun. 16, 2005

Related U.S. Application Data

(62) Division of application No. 09/828,648, filed on Apr. 6, 2001, now Pat. No. 6,689,877.

(60) Provisional application No. 60/246,331, filed on Nov. 6, 2000.

(51) Int. Cl.
 *C12Q 1/70* (2006.01)
(52) U.S. Cl. .................... 435/5; 435/7.1; 435/968; 435/974; 530/387.1; 530/388.1; 530/388.26; 530/389.2; 530/391.3
(58) Field of Classification Search .................... 435/5, 435/7.1, 968, 974; 530/387.1, 388.1, 388.26, 530/389.2, 391.3
See application file for complete search history.

(56) References Cited

U.S. PATENT DOCUMENTS 5,831,058 A * 11/1998 Fujiwara et al. ........... 536/23.5

FOREIGN PATENT DOCUMENTS

EP    0796913 A2 *  9/1997

OTHER PUBLICATIONS

Harlow et al. Antibodies: A Laboratory Manual. N.Y., Cold Spring Harbor, 1988. p. 353.*
Akiyama, Haruhiko. "Inflammatory Response in Alzheimer's Disease." *J. Exp. Med.* (1994) 295-303.
Bellefroid, Eric J., et al. "The Evolutionarily Conserved Kruppel-associated Box Domain Defines a Subfamily of Eukaryotic Multifingered Proteins." *Proc. Natl. Acad. Sci.* May 1991: 3608-3612.
Bernstein, Michael S., et al. "Activation of Human Monocyte-derived Macrophages with Lipopolysaccharide Decreases Human Immunodeficiency Virus Replication in Vitro at the Level of Gene Expression." *J. Clin. Invest.* vol. 88, Aug. 1991: 540-545.

Suio Chen, Robert C. A. Frederickson and Kurt R. Brunden. "Neuroglial-Mediated Immunoinflammatory Responses in Alzheimer's Disease: Complement Activation and Therapeutic Approaches." *Neurobiology of Aging.* vol. 17, No. 5, (1996) 781-787.
Cocchi, Fiorenza et. al. "Identification of RANTES, MIP-1α, and MIP-1β as the Major HIV-Suppressive Factors Produced by CD8+ T Cells." *Science.* vol. 270, Dec. 15, 1995: 1811-1815.
Elmquist, Joel K. "Mechanisms of CNS response to systemic immune challenge: the febrile response." *Tins.* vol. 20, No. 12, (1997) 565-570.
Evans, Ronald M. and Stanley M. Hollenberg. "Zinc Fingers: Gilt by Association." *Cell.* vol. 52, Jan. 15, 1988: 1-3.
Fauci, Anthony S. "Host factors and the pathogenesis of HIV-induced disease." *Nature.* vol. 384, Dec. 12, 1996: 529-534.
Franchin, Giovanni et al. "Lipoplysaccharide Inhibits HIV-1 Infection of Monocyte-Derived Macrophages Through Direct and Sustained Down-Regulation of CC Chemokine Receptor 5[1]." *The Journal of Immunology.* (2000) 2592-2601.
Haga, S. et al. "Demonstration of microglial cells in and around senile (neuritic) plaques in the Alzheimer brain." *Acta Neuropathologica.* vol. 77, (1989) 569-575.
Huitinga, Ingeborg. "Suppression of Experimental Allergic Encephalomyelitis in Lewis Rats After Elimination of Macrophages." *J. Exp. Med.* vol. 172, Oct. 1990: 1025-1033.
Imamoto, K. and C. P. Leblond. "Presence of Labeled Monocytes, Macrophages and Microglia in a Stab Wound of the Brain Following an Injection of Bone Marrow Cells Labeled with $^3$H-uridine into Rats." *Comp. Neuro.* vol. 174: 255-280.
Kadonaga, James T. et al. "Isolation of cDNA Encoding Transcription Factor Sp1 and Functional Analysis of the DNA Binding Domain." *Cell.* vol. 51, Dec. 24, 1987: 1079-1090.
Kornbluth, Richard S. "Interferons and Bacterial Lipopolysaccharide Protect Macrophages from Productive Infection by Human Immunodeficiency Virus in Vitro." *J. Exp. Med.* vol. 169, Mar. 1989: 1137-1151.
Lavi, Ehud. "CXCR-4 (Fusin), a Co-Receptor for the Type 1 Human Immunodeficiency Virus (HIV-1), Is Expressed in the Human Brain in a Variety of Cell Types, Including Microglia and Neurons." *American Journal of Pathology.* vol. 151, No. 4, Oct. 1997: 1035-1042.
Martin, Juan C. and Juan C. Bandres. "Cells of the Monocyte-Macrophage Lineage and Pathogenesis of HIV-1 Infection." *Journal of Acquired Immune Deficiency Syndromes.* vol. 22, (1999) 413-429.

(Continued)

*Primary Examiner*—Jeffrey Stucker
(74) *Attorney, Agent, or Firm*—Dann Dorfman Herrell and Skillman; Kathleen D. Rigaut

(57) ABSTRACT

Materials and methods are provided to inhibit HIV replication in targeted host cells.

9 Claims, 18 Drawing Sheets

OTHER PUBLICATIONS

S. Marty, I. Dusart and M. Peschanski. "Glial Changes Following an Excitotoxic Lesion in the CNS—I. Microglia/Macrophages." *Neuroscience*. vol. 45, No. 3, (1991) 529-539.

Saito, Hiroko et al. "Isolation and Mapping of a Novel Human Gene Encoding a Protein Containing Zinc-Finger Structures." *Genomics*. vol. 31, (1996) 376-379.

Schmidtmayerova, Helena et al. "Human Immunodeficiency Virus Type 1 T-Lymphotropic Strains Enter Macrophages via a CD4- and CXCR4-Mediated Pathway: Replication Is Restricted at a Postentry Level." *Journal of Virology*. Jun. 1998: 4633-4642.

Shannon, Mark et al. "Comparative Analysis of a Conserved Zinc Finger Gene Cluster on Human Chromosome 19q and Mouse Chromosome 7." *Genomics*. vol. 33, (1996) 112-120.

Sutcliffe, J. Gregor. "mRNA In the Mammalian Central Nervous System." *Ann. Rev. Neurosci*. vol. 11, (1988) 157-198.

Tan, Jun et al. "Microglial Activation Resulting from CD40-CD40L Interaction After β-Amyloid Stimulation." *Science*. vol. 286, Dec. 17, 1999: 2352-2355.

Thiesen, Hans-Jurgen and Wolfram Meyer. "Krab Domains Analyzed in Human Cys/His-Type Zinc-Finger Proteins KOX 1, KOX 8, and KOX $19^\alpha$." 243-245.

Witzgall, Ralph. "The Kruppel-associated box-A (KRAB-A) domain of zinc finger proteins mediates transcriptional repression." *Proc. Natl. Acad. Sci*. vol. 91, May 1994: 4514-4518.

Zybarth, Gabriele et al. "Activation-Induced Resistance of Human Macrophages to HIV-1 Infection In Vitro." *The Journal of Immunology*. vol. 162, (1999) 400-406.

Carlson, K. et al. "OTK18: A Surrogate Marker for HIV-1 Associated Dementia" (Abstract) $10^{th}$ Conference on Retroviruses and Opportunistic Infections. UNMC Feb. 2003.

Horiba, M. et al. "OTK18 Binds to Regulatory Elements of HIV-1 LTR and Regulates Transcriptional Activity" (Abstract) $10^{th}$ Conference on Retroviruses and Opportunistic Infections. UNMC Feb. 2003.

Limoges, J. et al. OTK18: A Transcriptional Suppresor Induced by HIV-1 Infection of Mononuclear Phagocytes and its Relevance to HIV-1 Dementia. (Abstract) $9^{th}$ Conference on Retroviruses and Opportunistic Infections. UNMC 2002.

* cited by examiner

Tissue Distribution of NEBR1 mRNA

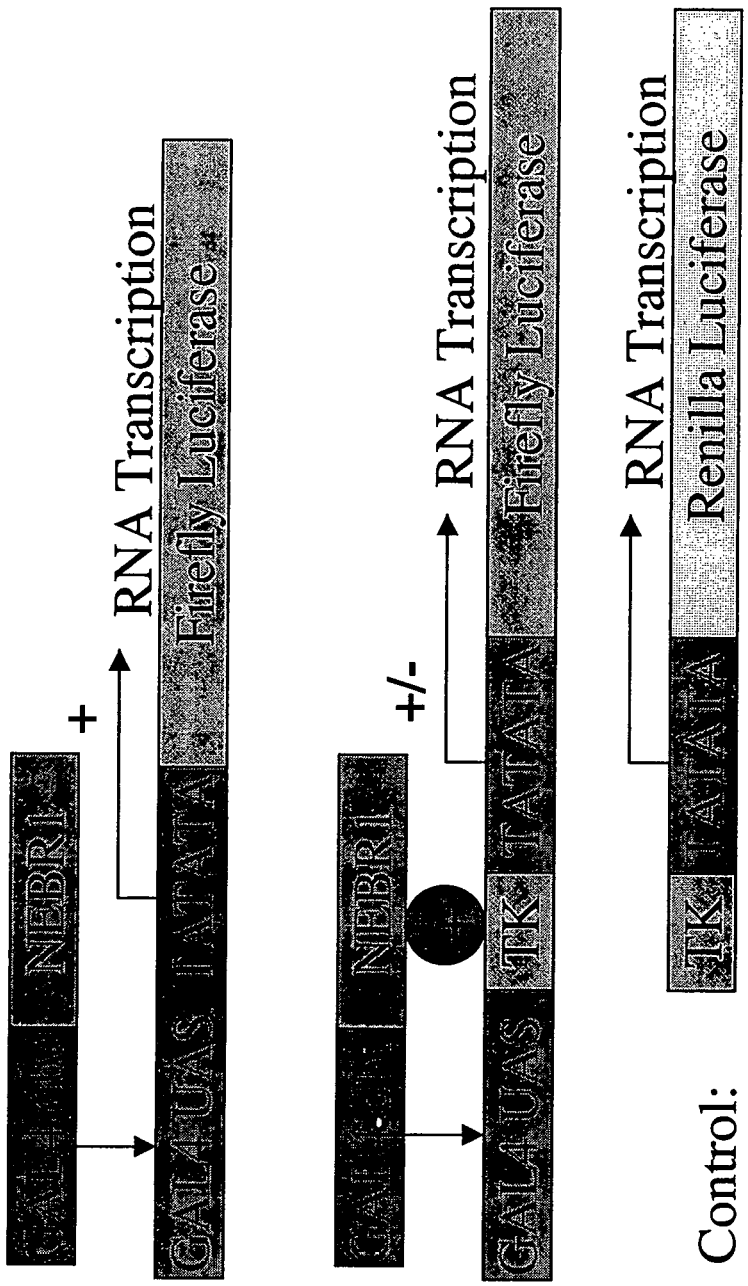

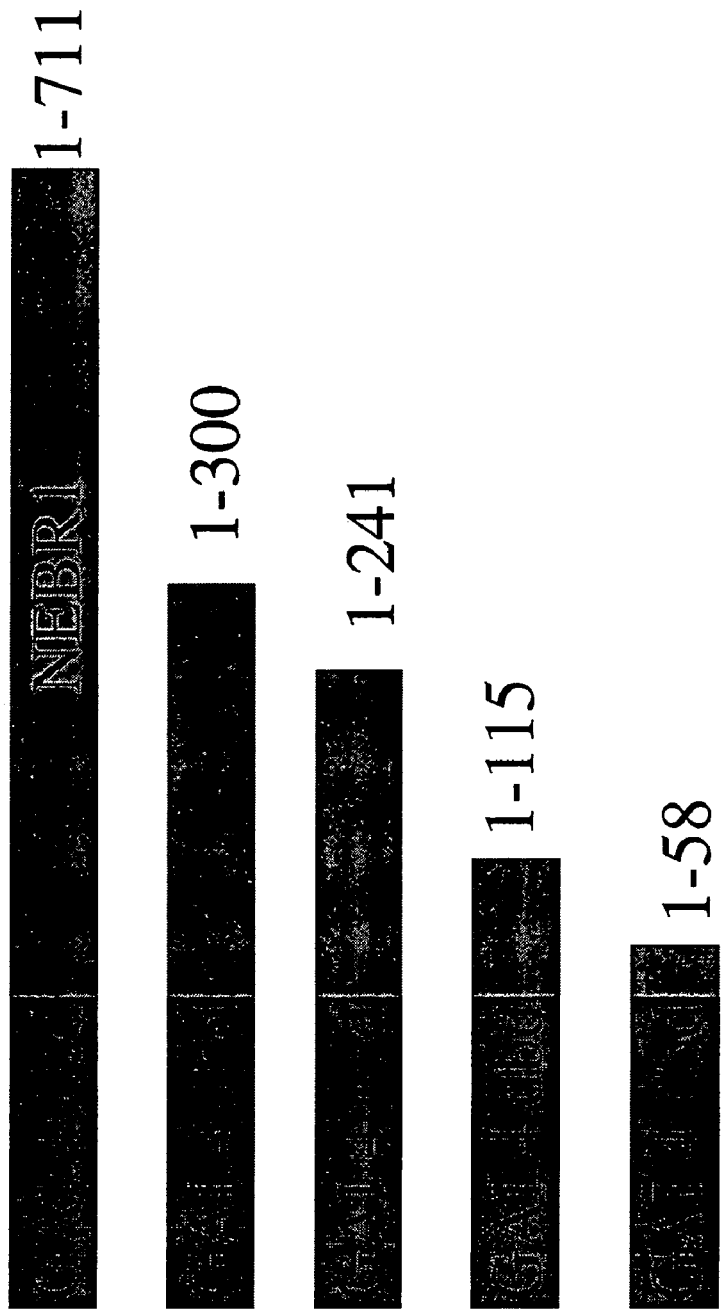

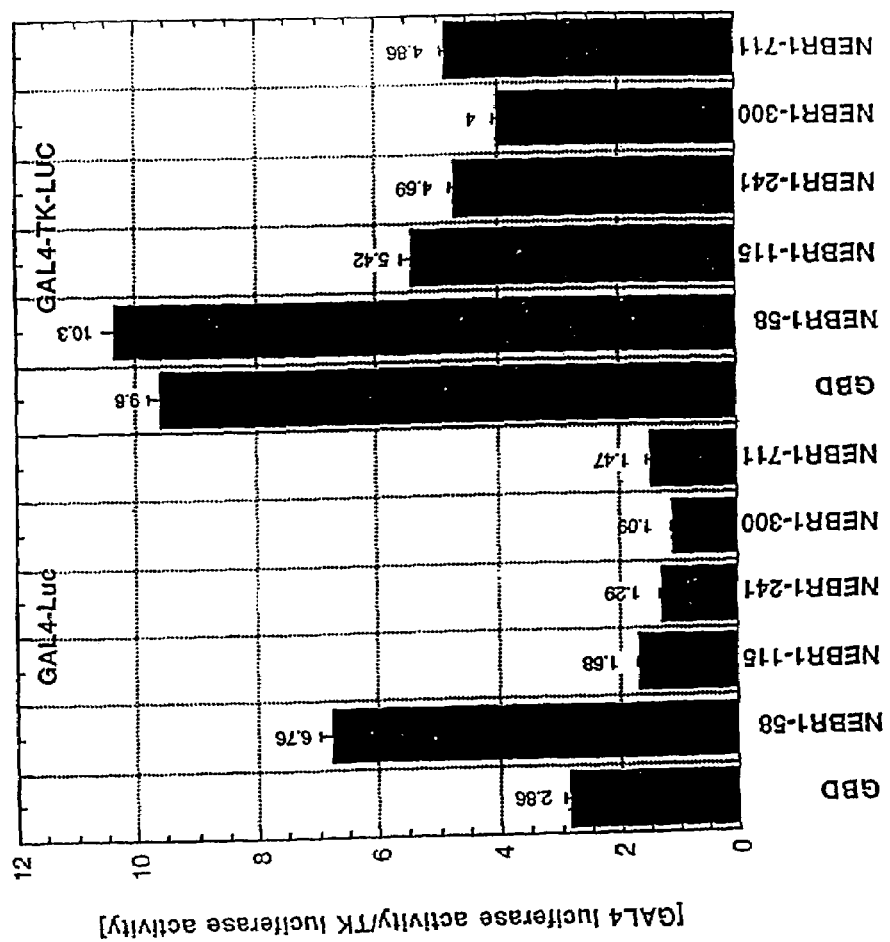
Fig. 4D Mutational analysis of NEBR1

Figure 5A

Multiple Sequence Alignment

KRAB-A

|   | 1 | | | | 50 |
|---|---|---|---|---|---|
| HSZNF41 | MAANGDSPPW | SPALAAEGRG | SSCEASVSFE | DVTVDFSKEE | WQHLDPAQRR |
| NEBR1 | MPADVNLSQK | PQVLGPEKQD | GSCEASVSFE | DVTVDFSREE | WQQLDPAQRC |
| KID1A | ~~~~~~~~~~ | ~~~MAPEQRE | GASQVSVTFE | DVAVLFTRDE | WKKLDLSQRS |
| ZNF157 | MPANGTSPQR | FPALIPGEPG | RSFEGSVSFE | DVAVDFTRQE | WHRLDPAQRT |
| GIOT-3 | ~~~~~~~~~~ | ~~~~~~~~~M | NKSLGPVSFK | DVAVDFTQEE | WQQLDPEQKI |
| RBAK | ~~~~~~~~~~ | ~~~~~~~~~M | NTLQGPVSFK | DVAVDFTQEE | WQQLDPDEKI |
| KS1 | ~~~~~~~~~~ | ~~~~~MNCHS | VPLQGPVSFK | DVTVDFTQEE | WQRLDPAQKA |

|   | 51 | KRAB-A | | KRAB-B | | KRAB-B1 | 100 |
|---|----|--------|--|--------|--|---------|-----|
| HSZNF41 | LYWDVTLENY | SHLLSV | GYQ | IPKSEAAFKL | EQGEGPWMLE | GEAPHQSCSG |
| NEBR1 | LYRDVMLELY | SHLFAV | GYH | IPNPEVIFRM | LKEKEPRVEE | AEVSHQRCQE |
| KID1A | LYREVMLENY | SNLASM | GFL | FTKPKVISLL | QQGEDPWQVE | KE..GPRYF. |
| ZNF157 | MHKDVMLETY | SNLASV | GLC | VAKPEMIFKL | ERGEELMILE | EESSGHGYSG |
| GIOT-3 | TYRDVMLENY | SNLVSV | GYH | IIKPDVISKL | EQGEEPMIVE | GEFLLQSYPD |
| RBAK | TYRDVMLENY | SHLVSV | GYD | TTKPNVIIKL | EQGEEPWIMG | GEFPCQHSP. |
| KS1 | LYRDVMLENY | CHFISV | GFH | ITKPDMIRKL | EQGEELW.TE | RMFPSQSYLE |

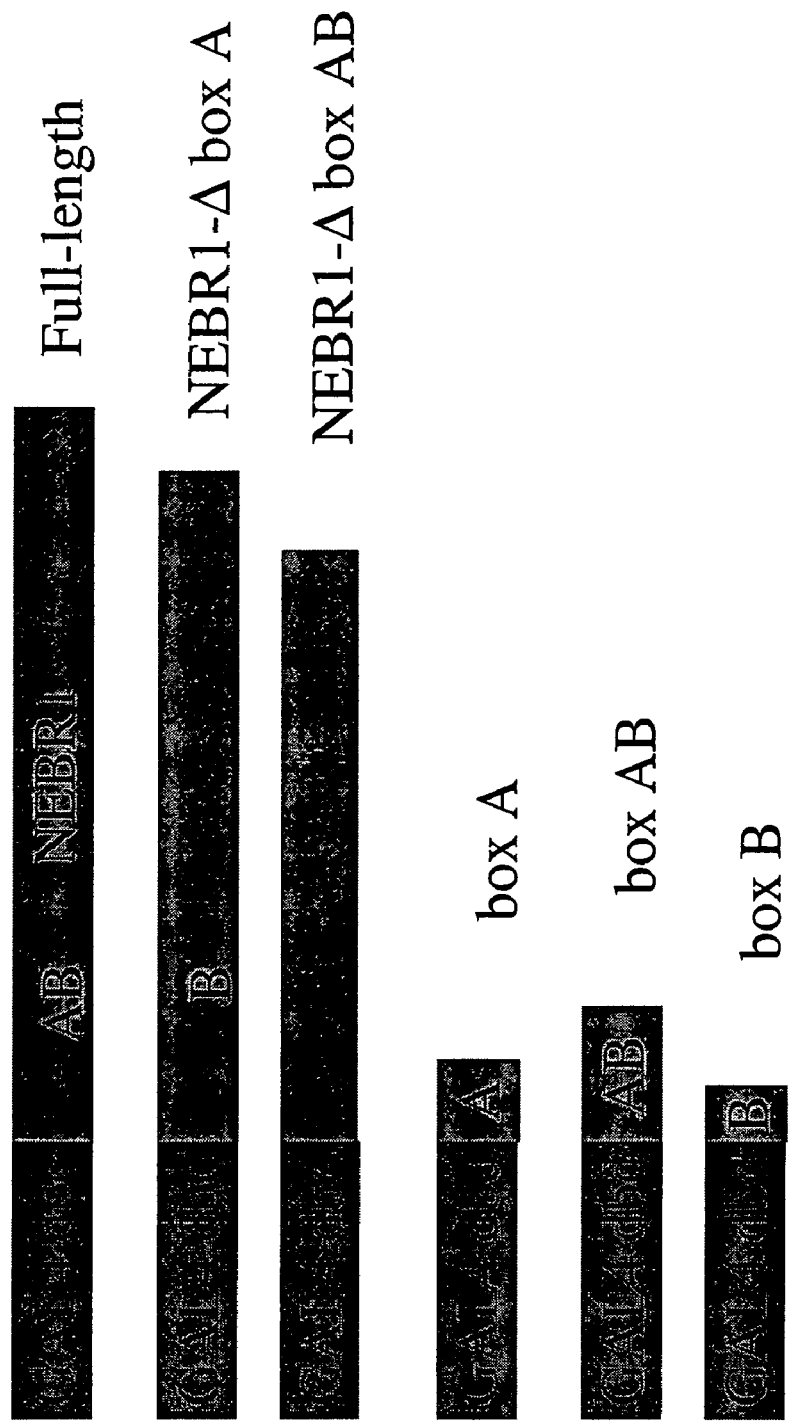

*NEBR1*:
Kruppel-associated box (KRAB)
containting transcription suppressor

Zinc finger, $C_2H_2$ type

KRAB

Multi-step inhibition mechanism by NEBR1

US 7,074,554 B2

ANTIBODIES SPECIFIC FOR NEBR1 AND METHODS OF USE THEREOF

This application is a Divisional Application of U.S. patent application Ser. No. 09/828,648 filed Apr. 6, 2001 now U.S. Pat. No. 6,689,877 which in turn claims priority to U.S. Provisional Application 60/246,331 filed Nov. 6, 2000. Each of the above identified application are incorporated herein by reference.

Pursuant to 35 U.S.C. §202(c) it is acknowledged that the U.S. Government has certain rights in the invention described herein, which was made in part with funds from the National Institutes of Health, Grant Numbers: 5 RO1 NS34239; 5 RO1 NS36126; and 5 RO1 NS36127.

FIELD OF THE INVENTION

This invention relates to the fields of molecular biology and virology. More specifically, the present invention provides materials and methods for inhibiting HIV infection in targeted host cells.

BACKGROUND OF THE INVENTION

Several publications are referenced in this application by author name, year and journal of publication in parentheses in order to more fully describe the state of the art to which this invention pertains. The disclosure of each of these publications is incorporated by reference herein.

Human Immunodeficiency Virus Type-1 (HIV-1)-associated dementia (HAD) is the result of cumulative pathogenic insults that ultimately affect brain synaptic function and neuronal death resulting in cognition and memory impairments. The mechanism by which functional changes occur in neurons during disease remains unknown. Nonetheless, neural injury correlates with immune activation of brain mononuclear phagocytes (MPs; infiltrating perivascular macrophages and resident brain macrophages or microglia). MPs are key mediators of central nervous system (CNS) inflammation. It is these cells that are recruited in response to trauma (12), infection, autoimmune reactions (11), and toxin (metabolic/drug) related injury (17). In the presence of an ongoing inflammatory response, both infiltrating macrophages and endogenous microglia become immune-activated. Activated MPs recruit additional leukocytes to sites of tissue injury and engage in a wide range of secretory activities. Such events may be mediated through chemokines and/or other inflammatory mediators that promote cellular adhesion and brain leukocyte infiltration. Importantly, MPs are capable of altering neuronal function/viability by disrupting the delicate homeostatic balance of the CNS microenvironment. Activated MP can generate cytotoxic factors that perpetuate paracrine-amplified inflammation (1, 4) leading to neuronal injury and loss.

The mechanism by which MPs become activated in the brain remains poorly understood but several lines of evidence indicate biochemical communication between the central nervous system and the immune system. It is likely that certain mechanisms involved in the CNS response to systemic immune challenge cause brain inflammation. Up- or down-regulation of gene expression of specific MP genes appears to mediate this process, leading to the culmination of a neurotoxic response and disease progression. Mammals have about 100,000 different genes, approximately 30,000 of which are thought to be expressed in the brain (21). Controlled regulation of gene expression ensures that small fractions of these genes are expressed in individual brain cells, gene expression being related to particular brain cell functions. It has been hypothesized that the pathological changes that arise in HAD are driven by aberrant changes in this regulated gene expression.

As those skilled in the treatment of HAD appreciate, a need exists for improved therapeutic agents for the treatment of this disorder.

SUMMARY OF THE INVENTION

In accordance with the present invention, methods and compositions for inhibiting HIV replication in host cells are provided. One embodiment of the invention comprises a nucleic acid encoding a truncated NEBR1 transcriptional repressor consisting essentially of amino acids 1–300 of SEQ ID NO: 2. Nucleic acids encoding truncated NEBR1 transcriptional repressors consisting essentially of amino acids 1–241 of SEQ ID NO: 2 or amino acids 1–115 of SEQ ID NO:2 are also provided herein.

In a further aspect of the invention, vectors containing the above-described nucleic acids are disclosed. The invention also encompasses transcriptional repressor of the invention. In a preferred embodiment, the host cell is a macrophage.

Truncated NEBR1 transcriptional repressor proteins are also within the scope of the invention. Such truncated NEBR1 proteins may be selected from the group consisting of amino acids 1–300 of SEQ ID NO: 2; amino acids 1–241 of SEQ ID NO: 2; and amino acids 1–115.

In another aspect of the invention, an antibody immunologically specific for NEBR1 is provided. Such antibodies may be monoclonal, polyclonal or antigen binding fragments of such antibodies.

Methods for detecting NEBR1 expression in a biological sample are also disclosed. Exemplary methods comprise contacting a sample with a detectably labeled antibody immunologically specific for NEBR1 and determining the presence of NEBR1 expression as a function of the amount of detectably labeled antibody bound by the sample relative to control cells.

In a further aspect of the invention methods for treating HIV infection comprising administering a therapeutic amount of NEBR1 to HIV infected cells in a patient in need thereof are provided. The NEBR1 so administered may be truncated or full-length. Such treatment methods may optionally comprise the administration of at least one antiviral agent selected from the group consisting of reverse transcriptase (RT) inhibitors, non-nucleoside inhibitors, and HIV-protease inhibitors.

BRIEF DESCRIPTION OF THE DRAWINGS

FIGS. 4A–4D show the results from analysis of NEBR1 Transcriptional Activity. FIG. 4A shows a schematic diagram of the DNA constructs used to assess the transcriptional suppressor activity of NEBR1. FIG. 4B shows that GBD-NEBR1 suppresses TK promoter-driven transcription. HEK 293 cells were transfected with pGBD-NEBR1 (0.1–0.6 μg), pGBD (0.1–0.6 μg), pTK-RL (0.1 μg), and either GAL4-Luc or GAL4-TK-Luc (0.3 μg) using Lipofectamine Plus. Twenty-four hours after transfection, cells were lysed and subjected to dual-luciferase assay. GBD-NEBR1 did not activate GAL4-Luc gene transcription, but suppressed GAL4-TK-Luc gene transcription of the transfected DNA in a dose-dependent manner for up to 54%. FIG. 4C shows the results of deletion mutant analysis of NEBR1 revealing that amino acids 58–115 are responsible for suppressive function. HEK293 cells were transfected with 0.6 μg of each pGBD-NEBR1 mutant, pTK-RL (0.1 μg) and either GAL-4 or GAL4-TK-Luc (0.3 μg) using Lipofectamine Plus. Twenty-four hours after transfection, cells were lysed and subjected to the dual-luciferase assay. Control GBD not GBD-NEBR1 (1–58) could suppress GAL4-TK-Luc gene transcription. GBD-NEBR1 (1–115, 1–241, and 1–300) suppressed gene transcription equal to full-length (1–711) constructs. The results depicted in FIG. 4D indicate that amino acids 58–115 are responsible for the suppressive function of NEBR1.

FIG. 5A shows the alignment of NEBR1 with other zinc finger proteins (the sequences are, from top to bottom: SEQ ID NO: 7, amino acids 1–99 of SEQ ID NO: 2, SEQ ID NO: 8, SEQ ID NO: 9, SEQ ID NO: 10, SEQ ID NO: 11, and SEQ ID NO: 12). FIGS. 5B and 5C show the transcriptional activity of KRAB box mutants of NEBR1. HEK293 cells were transfected with 0.6 μg of each pGBD-NEBR1 mutant and either GAL4-Luc or GAL4-TK-Luc (0.3 g) using Lipofectamine Plus. Twenty-four hours after transfection, cells were lysed and subjected to dual-luciferase assay. Control GBD not GBD Box ΔB could suppress GAL4-TK-Luc gene transcription. GBD Box ΔA partially suppressed the gene transcription, however the other mutants suppressed it as potent as full-length NEBR1.

FIG. 6A shows the constructs used for this analysis. FIG. 6B shows that PSV2-Tat activated LTR-Luc gene transcription, but was suppressed by the co-transfection of pCDNA-NEBR1 for up to 80%. Control plasmid (pCDNA3) had no effect on LTR-Luc activity with or without co-transfection of pSV2-Tat.

DETAILED DESCRIPTION OF THE INVENTION

Figure 1:
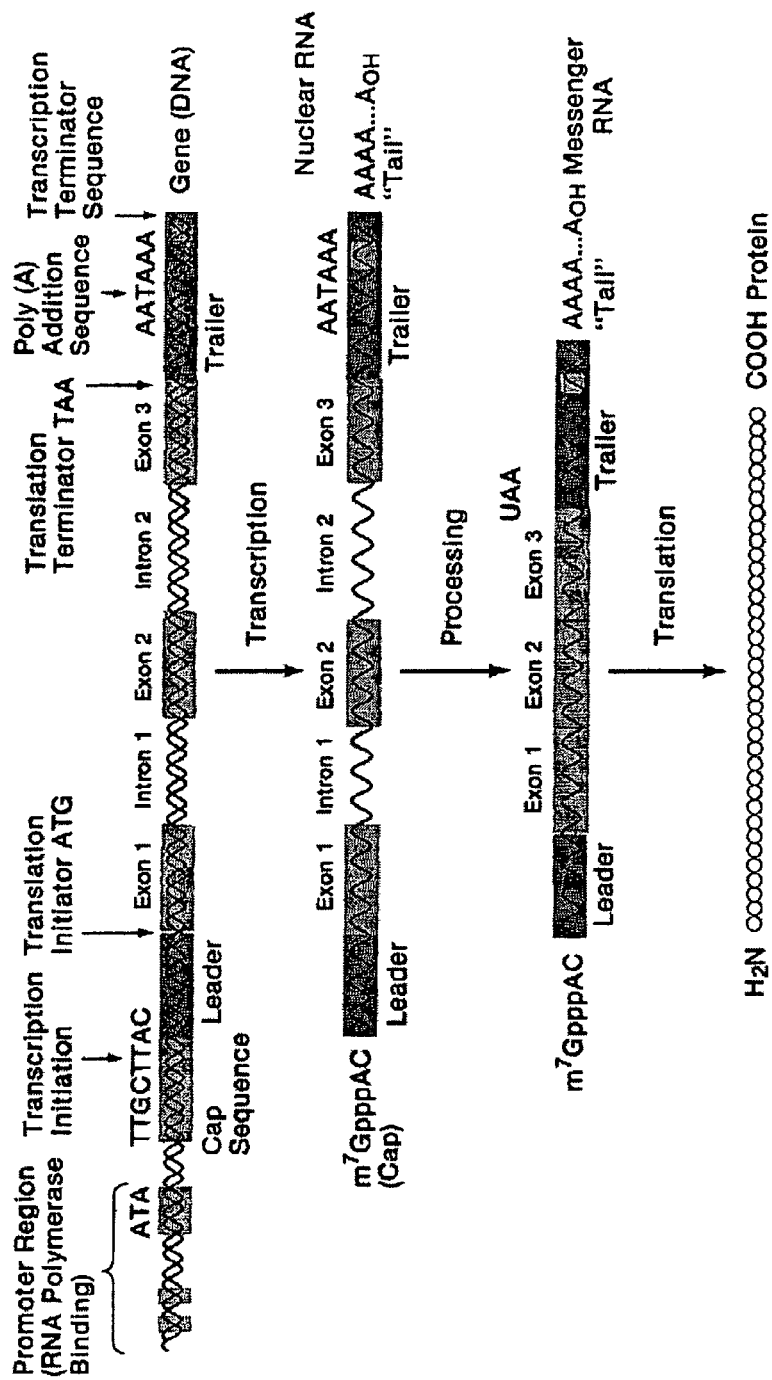
FIG. 1 depicts a schematic drawing of the genomic structure of the NEBR1 gene (also known as OTK18, GenBank Accession Nos: AC018755 and AC020914). NEBR1 contains 13 $C_2H_2$ type zinc finger motifs indicative of its function as a transcriptional regulator. The NEBR1 gene is located on chromosome 19q13.4.

Many neurodegenerative disorders, notably Alzheimer's disease, (AD) and HIV-1-associated dementia, (HAD), demonstrate mononuclear phagocyte (MP) activation as a principal component of tissue pathology. In attempts to ascertain biologically relevant MP products that influence neurodestructive processes differential display technologies were utilized and cDNA libraries prepared from activated and/or HIV-1 infected monocyte-derived macrophages (MDM). MDM RNA was prepared and differentially expressed genes were recovered. Recombinant DNAs recovered were cloned into pCR-TRAP, sequenced and assessed by GenBank analyses. DNA primers were constructed and human HAD and AD pathologic brain tissues used to analyze gene expression. These works led to the discovery of NEBR1 and its function as a putative transcriptional factor; it contains 13 adjacent $C_2H_2$ type zinc finger motifs.

NEBR1 expression was analyzed by immunoblotting and immunohistochemistry on MDM cell suspensions and brain tissue (AD, HAD, and control brains). AD and HAD showed high levels of NEBR1 expression. Both cytoplasmic and nuclear staining were present in activated and/or HIV-1 infected MDM. The transcriptional activity of NEBR1 was tested in a GAL4-DNA binding fusion protein assay. NEBR1 suppressed thymidine kinase driven gene transcription in a dose-dependent manner; implicating it as a transcriptional suppressor. These results reveal that NEBR1 is a transcriptional regulator activated in MP during diverse neurodegenerative disorders.

I. Definitions

Various terms relating to the biological molecules of the present invention are used hereinabove and also throughout the specifications and claims. The terms "specifically hybridizing," "percent similarity" and "percent identity (identical)" are defined in detail in the description set forth below.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The phrase "consisting essentially of" when referring to a particular nucleotide or amino acid means a sequence having the properties of a given SEQ ID No:. For example, when used in reference to an amino acid sequence, the phrase includes the sequence per se and molecular modifications that would not affect the basic and novel characteristics of the sequence.

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to antibodies of the invention, the term "immunologically specific" refers to antibodies that bind to one or more epitopes of a protein or interest (e.g., NEBR1), but which do not substantially recognize and bind other molecules in a sample containing a mixed population and antigenic biological molecules.

An "antibody" or "antibody molecule" is any immunoglobulin, including antibodies and fragments thereof, that binds to a specific antigen. The term includes polyclonal, monoclonal, chimeric, and bispecific antibodies. As used herein, antibody or antibody molecule contemplates both an intact immunoglobulin molecule and an immunologically active portion of an immunloglobulin molecule such as those portions known in the art as Fab, Fab', F(ab')2 and F(v).

With respect to oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The present invention also includes active portions, fragments, derivatives and functional mimetics of the NEBR1 polypeptide or protein of the invention.

An "active portion" of NEBR1 polypeptide means a peptide which is less than said full length NEBR1 polypeptide, but which retains its essential biological activity, e.g., transcription regulating activity.

A "fragment" of the NEBR1 polypeptide means a stretch of amino acid residues of at least about five to seven contiguous amino acids, often at least about seven to nine contiguous amino acids, typically at least about nine to thirteen contiguous amino acids and, most preferably, at least about twenty to thirty or more contiguous amino acids. Fragments of the NEBR1 polypeptide sequence, antigenic determinants or epitopes are useful for raising antibodies to a portion of the NEBR1 amino acid sequence.

A "derivative" of the NEBR1 polypeptide or a fragment thereof means a polypeptide modified by varying the amino acid sequence of the protein, e.g. by manipulation of the nucleic acid encoding the protein or by altering the protein itself. Such derivatives of the natural amino acid sequence may involve insertion, addition, deletion or substitution of one or more amino acids, without fundamentally altering the essential activity of the wildtype NEBR1 polypeptide.

"Functional mimetic" means a substance which may not contain an active portion of the NEBR1 amino acid sequence, and probably is not a peptide at all, but which retains the essential biological activity of natural NEBR1 polypeptide.

A "promoter" is a DNA sequence located proximal to the start of transcription at the 5' end of an operably linked transcribed sequence. The promoter may contain one or more regulatory elements or modules which interact in modulating transcription of the operably linked gene.

"Operably linked" describes two macromolecular elements arranged such that modulating the activity of the first element induces an effect on the second element. In this manner, modulation of the activity of a promoter element may be used to alter and/or regulate the expression of an operably-linked coding sequence. For example, the transcription of a coding sequence that is operably-linked to a promoter element is induced by factors that "activate" the promoter's activity; transcription of a coding sequence that is operably-linked to a promoter element is inhibited by factors that "repress" the promoter's activity. Thus, a promoter region is operably-linked to the coding sequence of a protein if transcription of such coding sequence activity is influenced by the activity of the promoter.

As used herein, an "expression vector" is a vector especially designed to provide an environment which allows the expression of the cloned gene after transformation into the host. One manner of providing such an environment is to include transcriptional and translational regulatory sequences on such expression vehicle, such transcriptional and translational regulatory sequences being capable of being operably linked to the cloned gene. Another manner of providing such an environment is to provide a cloning site or sites on such vehicle, wherein a desired cloned gene and desired expression regulatory elements may be cloned.

In an expression vector, the gene to be cloned is usually operably-linked to certain control sequences such as promoter sequences. Expression control sequences will vary depending on whether the vector is designed to express the operably-linked gene in a prokaryotic or eukaryotic host and may additionally contain transcriptional elements such as enhancer elements, termination sequences, tissue-specificity elements, and/or translational initiation and termination sites.

The following sequences have been utilized in the present invention:

```
   1 gctaagccta tgtcgcttac tggacgctga agtgattggg aatattagca gtggggttc   SEQ ID NO: 1
  61 tgtagggtca ggaaggggcg gctggctttg ggggagtgat gagggcttg ttggggtgg
 121 gggtgcgtga taaagggatt tctcggctga agacgaggct gtgaggcttc tgcagaaccc
 181 ccaggtcagg ccacatcatt gaggctgcag gatctctctt catagcccag tacgactctc
 241 cgccgtgtcc ctggttggaa aatccaaaca cctatccagc ttctggctcc tgggaaaagt
 301 ggagttgtca gcaagagaga ccgagagtag aagcccagag tggagatgcc tgctgatgtg
 361 aatttatccc agaagcctca ggtcctgggt ccagagaagc aggatggatc ttgcgaggca
 421 tcagtgtcat ttgaggacgt gaccgtggac ttcagcaggg aggagtggca gcaactggac
 481 cctgcccaga gatgcctgta ccgggatgtg atgctggagc tctatagcca tctcttcgca
 541 gtggggtatc acattcccaa cccagaggtc atcttcagaa tgctaaaaga aaaggagccg
 601 cgtgtggagg aggctgaagt ctcacatcag aggtgtcaag aaagggagtt tgggcttgaa
 661 atcccacaaa aggagatttc taagaaagct tcatttcaaa aggatatggt aggtgagttc
 721 acaagagatg gttcatggtg ttccatttta gaagaactga ggctggatgc tgaccgcaca
 781 aagaaagatg agcaaaatca aattcaaccc atgagtcaca gtgctttctt caacaagaaa
 841 acattgaaca cagaaagcaa ttgtgaatat aaggaccctg ggaaaatgat tcgcacgagg
 901 ccccacccttg cttcttcaca gaaacaacct cagaaatgtt gcttatttac agaaagtttg
 961 aagctgaacc tagaagtgaa cggtcagaat gaaagcaatg acacagaaca gcttgatgac
1021 gttgttgggt ctggtcagct attcagccat agctcttctg atgcctgcag caagaatatt
1081 catacaggag agacattttg caaaggtaac cagtgtagaa aagtctgtgg ccataaacag
1141 tcactcaagc aacatcaaat tcatactcag aagaaaccag atggatgttc tgaatgtggg
1201 gggagcttca cccagaagtc acacctcttt gcccaacaga gaattcatag tgtaggaaac
1261 ctccatgaat gtggcaaatg tggaaaagcc ttcatgccac aactaaaact cagtgtatac
1321 ctgacagatc atacaggtga tatccctgt atatgcaagg aatgtgggaa ggtctttatt
1381 cagagatcag aattgcttac gcaccagaaa acacacacta gaaagaagcc ctataaatgc
1441 catgactgtg gaaaagcctt tttccagatg ttatctctct tcagacatca gagaactcac
1501 agtagagaaa aactctatga atgcagtgaa tgtggcaaag gcttctccca aaactcaacc
1561 ctcattatac atcagaaaat tcatactggt gagagacagt atgcatgcag tgaatgtggg
1621 aaagccttta cccagaagtc aacactcagc ttgcaccaga gaatccactc agggcagaag
1681 tcctatgtgt gtatcgaatg cgggcaggcc ttcatccaga aggcacacct gattgtccat
1741 caaagaagcc acacaggaga aaaaccttat cagtgccaca actgtgggaa atccttcatt
1801 tccaagtcac agcttgatat acatcatcga attcatacag gggagaaacc ttatgaatgc
1861 agtgactgtg gaaaaacctt cacccaaaag tcacacctga atatacacca gaaaattcat
1921 actggagaaa gacaccatgt atgcagtgaa tgcgggaaag ccttcaacca gaagtcaata
```

```
1981 ctcagcatgc atcagagaat tcacaccgga gagaagcctt acaaatgcag tgaatgtggg
2041 aaagccttca cttctaagtc tcaattcaaa gagcatcagc gaattcacac gggtgagaaa
2101 ccctatgtgt gcactgaatg tgggaaggcc ttcaacggca ggtcaaattt ccataaacat
2161 caaataactc acactagaga gaggcctttt gtctgttaca aatgtgggaa ggcttttgtc
2221 cagaaatcag agttgattac ccatcaaaga actcacatgg gagagaaacc ctatgaatgc
2281 cttgactgtg ggaaatcgtt cagtaagaaa ccacaactca aggtgcatca gcgaattcac
2341 acgggagaaa gaccttatgt gtgttctgaa tgtggaaagg ccttcaacaa caggtcaaac
2401 ttcaataaac accaaacaac tcataccaga gacaaatctt acaaatgcag ttattctgtg
2461 aaaggcttta ccaagcaatg aattcctagt gcatcagcat attcataaat gaaatatact
2521 ccgagtttct tgaagaagag aacatcttct cagaatcagg tctaattata tgttattgaa
2581 ttcatgcttc agaaaaactc tagggatgca ctgcatgtgt aacacatga taaaaaagtc
2641 atgctttatt ttagtgaggg caattacaga gaaaagagta agcagaaatg tccttctgag
2701 tactggcctc attaaggatt ataaattttc tccccgggaa gaaaccctga ctaacgcatt
2761 gagaaaagcc tttctgtaaa gaatggtaca agacaggttg ttactcgatt atttatagta
2821 aaatatgtgg gaattatat caatgataac cctgtttatt gtgggatatc aatattttta
2881 aagtgccaac acagtcatga taggacaata ttttatgtgt gtgtgtgcgc ttatgtata
2941 taagcatata tataatatat aagcatatta ttatatacag gttgagtatc ccttctccaa
3001 aatgcctggg atcagaagca ttttggattt cagatactta cagattttgg aatatttgca
3061 ttatatttat tggttgagca tccctaatct gaaaatccaa gattaaatgc tccaattagc
3121 atttcctttg agcgtcatgt tagagttcaa aaagtttcag attttgggtt ttcagattag
3181 gaatacccaa cctgtatgta cgtatatttc tgtatctatg tatgtatata tatgcatatg
3241 cagacatatg tatatggtct ggtcagcata tgtgtatgta tgcgtatgta tgtatgtatg
3301 tatgccctca gtgcagtggg gtttgctgca gaattcactg catagcagga gatgtaagca
3361 gatgagttat tttttaagag aatctaatct aattgttttt ataaaaatta ttccctattg
3421 aatatttata taatgaggtt gtatcaacaa tgattaactc ctttattata catacacatg
3481 aatgtgcatt tttggtaaat gcataaatga gattctataa tgtttactga tctttatatt
3541 acagattttc tcttctttta ggattagctc agcttgcccc cccttccat ctccaccatc
3601 tatagtgagc ctctccataa ttagtgccaa ccattagtct cgttcatatt tttacaccag
3661 gagtcaacaa actgtgccat tggccaaata tggcctccca actgtttttt taaaataaag
3721 ttttattgga acac
```

MPADVNLSQKPQVLGPEKQDGSCEASVSFEDVTVDFSREEWQQLDPAQRCLYRDVMLELYSHLFAVGYHI SEQ ID NO: 2

PNPEVIFRMLKEKEPRVEEAEVSHQRCQEREFGLEIPQKEISKKASFQKDMVGEFTRDGSWCSILEELRL

DADRTKKDEQNQIQPMSHSAFFNKKTLNTESNCEYKDPGKMIRTRPHLASSQKQPQKCCLFTESLKLNLE

VNGQNESNDTEQLDDVVGSGQLFSHSSSDACSKNIHTGETFCKGNQCRKVCGHKQSLKQHQIHTQKKPDG

CSECGGSFTQKSHLFAQQRIHSVGNLHECGKCGKAFMPQLKLSVYLTDHTGDIPCICKECGKVFIQRSEL

LTHQKTHTRKKPYKCHDCGKAFFQMLSLFRHQRTHSREKLYECSECGKGFSQNSTLIIHQKIHTGERQYA

CSECGKAFTQKSTLSLHQRIHSGQDSYVCIECGQAFIQKAHLIVHQRSHTGEKPYQCHNCGKSFISKSQL

DIHHRIHTGEKPYECSDCGKTFTQKSHLNIHQKIHTGERHHVCSECGKAFNQKSILSMHQRIGTGEKPYD

CSECGKAFTSKSQFKEHQRIGTGEKPYVCTECGKAFNGRSNFHKHQITHTRERPFVCYKCGKAFVQKSEL

-continued
ITHQRTHMGEKPYECLDCGKSFSKKPQLKVHQRIHTGERPYVCSECGKAFNNRSNFNKHQTTHTRDKSYK

CSYSVKGFTKQ

Preparation of NEBR1-Encoding Nucleic Acid Molecules, NEBR1 Proteins, and Antibodies Thereto A. Nucleic Acid Molecules Nucleic acid molecules encoding the NEBR1 transcriptional regulator of the invention may be prepared by two general methods: (1) Synthesis from appropriate nucleotide triphosphates, or (2) Isolation from biological sources. Both methods utilize protocols well known in the art.

The availability of nucleotide sequence information, such as the full length cDNA having Sequence I.D. No. 1, enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 2.4 kb double-stranded molecule may be synthesized as several smaller segments of appropriate sequence. Complementary segments thus produced may be annealed such that each segment possesses appropriate cohesive termini for attachment of an adjacent segment. Adjacent segments may be ligated by annealing cohesive termini in the presence of DNA ligase to construct an entire 2.4 kb double-stranded molecule. A synthetic DNA molecule so constructed may then be cloned and amplified in an appropriate vector.

Nucleic acid sequences encoding NEBR1 may be isolated from appropriate biological sources using methods known in the art. In a preferred embodiment, a cDNA clone is isolated from a cDNA expression library of human origin. In an alternative embodiment, utilizing the sequence information provided by the cDNA sequence, genomic clones encoding NEBR1 may be isolated. Alternatively, cDNA or genomic clones having homology with NEBR1 may be isolated from other species, such as mouse, using oligonucleotide probes corresponding to predetermined sequences within the NEBR1 gene.

In accordance with the present invention, nucleic acids having the appropriate level of sequence homology with the protein coding region of Sequence I.D. No. 1 may be identified by using hybridization and washing conditions of appropriate stringency. For example, hybridizations may be performed, according to the method of Sambrook et al., (supra) using a hybridization solution comprising: 5X SSC, 5X Denhardt's reagent, 0.5–1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2X SSC and 0.5–1% SDS; (2) 15 minutes at room temperature in 2X SSC and 0.1% SDS; (3) 30 minutes–1 hour at 37° C. in 1X SSC and 1% SDS; (4) 2 hours at 42–65° in 1X SSC and 1% SDS, changing the solution every 30 minutes.

One common formula for calculating the stringency conditions required to achieve hybridization between nucleic acid molecules of a specified sequence homology is (Sambrook et al., 1989): $T_m = 81.5° + 16.6$ Log $[Na+] + 0.41$ (5 G+C)–0.63 (% formamide)–600/#bp in duplex As an illustration of the above formula, using $[Na+] = [0.368]$ and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

Nucleic acids of the present invention may be maintained as DNA in any convenient cloning vector. In a preferred embodiment, clones are maintained in a plasmid cloning/expression vector, such as pBluescript (Stratagene, La Jolla, Calif.), which is propagated in a suitable E. coli host cell. Genomic clones of the invention encoding the human or mouse NEBR1 gene may be maintained in lambda phage FIX II (Stratagene).

NEBR1-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the cDNA having Sequence I.D. No. 1. Such oligonucleotides are useful as probes for detecting or isolating NEBR1 genes.

It will be appreciated by persons skilled in the art that variants (e.g., allelic variants) of these sequences exist in the human population, and must be taken into account when designing and/or utilizing oligos of the invention. Accordingly, it is within the scope of the present invention to encompass such variants, with respect to the NEBR1 sequences disclosed herein or the oligos targeted to specific locations on the respective genes or RNA transcripts. With respect to the inclusion of such variants, the term "natural allelic variants" is used herein to refer to various specific nucleotide sequences and variants thereof that would occur in a human population. Genetic polymorphisms giving rise to conservative or neutral amino acid substitutions in the encoded protein are examples of such variants. Additionally, the term "substantially complementary" refers to oligo sequences that may not be perfectly matched to a target sequence, but the mismatches do not materially affect the ability of the oligo to hybridize with its target sequence under the conditions described.

Thus, the coding sequence may be that shown in Sequence I.D. No. 1, or it may be a mutant, variant, derivative or allele of this sequence. The sequence may differ from that shown by a change which is one or more of addition, insertion, deletion and subsitution of one or more nucleotides of the sequence shown. Changes to a nucleotide sequence may result in an amino acid change at the protein level, or not, as determined by the genetic code.

Thus, nucleic acid according to the present invention may include a sequence different from the sequence shown in Sequence I.D. No. 1 yet encode a polypeptide with the same amino acid sequence.

On the other hand, the encoded polypeptide may comprise an amino acid sequence which differs by one or more amino acid residues from the amino acid sequence shown in Sequence I.D. No. 2. Nucleic acid encoding a polypeptide which is an amino acid sequence mutant, variant, derivative or allele of the sequence shown in Sequence I.D. No. 2 is further provided by the present invention. Nucleic acid encoding such as polypeptide may show greater than 60% homology with the coding sequence shown in Sequence I.D. No. 1, greater than about 70% homology, greater than about 80% homology, greater than about 90% homology or greater than about 95% homology.

Also within the scope of the invention are antisense oligonucleotide sequences based on the NEBR1 nucleic acid sequences described herein. Antisense oligonucleotides may be designed to hybridize to the complementary sequence of nucleic acid, pre-mRNA or mature mRNA, interfering with the production of polypeptides encoded by a given DNA sequence (e.g. either native NEBR1 polypeptide or a mutant form thereof), so that its expression is reduced or prevented altogether. In addition to the NEBR1 coding sequence, antisense techniques can be used to target control sequences of the NEBR1 gene, e.g. in the 5' flanking sequence of the NEBR1 coding sequence, whereby the antisense oligonucleotides can interfere with NEBR1 control sequences. The construction of antisense sequences and their use is described in Peyman and Ulman, Chemical Reviews, 90:543–584, (1990), Crooke, Ann. Rev. Pharmacol. Toxical., 32:329–376, (1992), and Zamecnik and Stephenson, Proc. Natl. Acad. Sci., 75:280–284, (1974).

The present invention provides a method of obtaining nucleic acid of interest, the method including hybridization of a probe having part or all of the sequence shown in Sequence I.D. No. 1 or a complementary sequence, to target nucleic acid. Hybridization is generally followed by identification of successful hybridization and isolation of nucleic acid which has hybridized to the probe, which may involve one or more steps of PCR.

In some preferred embodiments, oligonucleotides according to the present invention that are fragments of the sequences shown in Sequence I.D. No. 1 are at least about 10 nucleotides in length, more preferably at least 15 nucleotides in length, more preferably at least about 20 nucleotides in length. Such fragments themselves individually represent aspects of the present invention. Fragments and other oligonucleotides may be used as primers or probes as discussed but may also be generated (e.g. by PCR) in methods concerned with suppressing gene expression in HIV infected test samples.

Nucleic acid according to the present invention may be used in methods of gene therapy, for instance in treatment of individuals with the aim of preventing or curing (wholly or partially) HAD. This too is discussed below.

B. Proteins

NEBR1 protein contains 13 $C_2 H_2$ type zinc finger motifs implicating it as a transcriptional regulator. A full-length or truncated NEBR1 protein of the present invention may be prepared in a variety of ways, according to known methods. The protein may be purified from appropriate sources, e.g., transformed bacterial or animal cultured cells or tissues, by immunoaffinity purification. However, this is not a preferred method due to the low amount of protein likely to be present in a given cell type at any time. The availability of nucleic acid molecules encoding NEBR1 enables production of the protein using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or BRL, Rockville, Md.

Alternatively, according to a preferred embodiment, larger quantities of full length or truncated NEBR1 may be produced by expression in a suitable prokaryotic or eukaryotic system. For example, part or all of a DNA molecule, such as the cDNA having Sequence I.D. No. 1, may be inserted into a plasmid vector adapted for expression in a bacterial cell, such as E. coli. Such vectors comprise the regulatory elements necessary for expression of the DNA in the host cell (e.g. E. coli) positioned in such a manner as to permit expression of the DNA in the host cell. Such regulatory elements required for expression include promoter sequences, transcription initiation sequences and, optionally, enhancer sequences.

The NEBR1 produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6–8 histidine residues at their N-terminus or C-terminus. Alternative tags may comprise the FLAG epitope or the hemagglutinin epitope. Such methods are commonly used by skilled practitioners.

The NEBR1 proteins of the invention, prepared by the aforementioned methods, may be analyzed according to standard procedures. For example, such proteins may be subjected to amino acid sequence analysis, according to known methods.

As discussed above, a convenient way of producing a polypeptide according to the present invention is to express nucleic acid encoding it, by use of the nucleic acid in an expression system. The use of expression systems has reached an advanced degree of sophistication today.

Accordingly, the present invention also encompasses a method of making a polypeptide (as disclosed), the method including expression from nucleic acid encoding the polypeptide (generally nucleic acid according to the invention). This may conveniently be achieved by growing a host cell in culture, containing such a vector, under appropriate conditions which cause or allow production of the polypeptide. Polypeptides may also be produced in in vitro systems, such as reticulocyte lysate.

Polypeptides which are amino acid sequence variants, alleles, derivatives or mutants are also provided by the present invention. A polypeptide which is a variant, allele, derivative, or mutant may have an amino acid sequence that differs from that given in Sequence I.D. No. 2 by one or more of addition, substitution, deletion and insertion of one or more amino acids. Preferred such polypeptides have NEBR1 function, that is to say have one or more of the following properties: the ability to bind DNA; inhibit transcription of target genes; immunological cross-reactivity with an antibody reactive with the polypeptide for which the sequence is given in Sequence I.D. No. 2; sharing an epitope with the polypeptide for which the sequence is given in Sequence I.D. No. 2 (as determined for example by immunological cross-reactivity between the two polypeptides.

A polypeptide which is an amino acid sequence variant, allele, derivative or truncation of the amino acid sequence shown in Sequence I.D. No. 2 may comprise an amino acid sequence which shares greater than about 35% sequence identity with the sequence shown, greater than about 40%, greater than about 50%, greater than about 60%, greater than about 70%, greater than about 80%, greater than about 90% or greater than about 95%. Particular amino acid sequence variants may differ from that shown in Sequence I.D. No. 2 by insertion, addition, substition or deletion of 1 amino acid, 2, 3, 4, 5–10, 10–20, 20–30, 30–40, 40–50, 50–100, 100–150, or more than 150 amino acids.

A polypeptide according to the present invention may be used in screening for molecules which affect or modulate its activity or function. Such molecules may be useful in a therapeutic (possibly including prophylactic) context.

The present invention also provides antibodies capable of immunospecifically binding to proteins of the invention. Polyclonal antibodies directed toward NEBR1 may be prepared according to standard methods. In a preferred embodiment, monoclonal antibodies are prepared, which react immunospecifically with various epitopes of NEBR1. Monoclonal antibodies may be prepared according to general methods of Köhler and Milstein, following standard protocols. Polyclonal or monoclonal antibodies that immunospecifically interact with NEBR1 can be utilized for identifying and purifying such proteins. For example, antibodies may be utilized for affinity separation of proteins with which they immunospecifically interact. Antibodies may also be used to identify multinuclear giant cells in HIV encephalitic brains or immune activated MP in the brains, or for FACS analysis of peripheral blood cells to evaluate the antiretroviral reaction of MP. NEBR1-specific antibodies may also be used to immunoprecipitate proteins from a sample containing a mixture of proteins and other biological molecules. Other uses of anti-NEBR1 antibodies are described below.

Antibodies according to the present invention may be modified in a number of ways. Indeed the term "antibody" should be construed as covering any binding substance having a binding domain with the required specificity. Thus, the invention covers antibody fragments, derivatives, functional equivalents and homologues of antibodies, including synthetic molecules and molecules whose shape mimics that of an antibody enabling it to bind an antigen or epitope.

Exemplary antibody fragments, capable of binding an antigen or other binding partner, are Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

Humanized antibodies in which CDRs from a non-human source are grafted onto human framework regions, typically with alteration of some of the framework amino acid residues, to provide antibodies which are less immunogenic than the parent non-human antibodies, are also included within the present invention.

II. Uses of NEBR1-Encoding Nucleic Acids, NEBR1 Proteins and Antibodies Thereto

NEBR1 appears to be a transcriptional regulator which is upregulated HIV-1 dementia and other neuronal disorders. The NEBR1 molecules of the invention may be used to advantage in methods for the treatment and diagnosis of HIV infection.

Additionally, NEBR1 nucleic acids, proteins and antibodies thereto, according to this invention, may be used as research tools to identify other proteins that are intimately involved the control of gene expression in response to HIV infection and subsequent neuronal injury. Biochemical elucidation of the transcriptional suppressor activity of NEBR1 will facilitate the development of novel assays for controlling aberrant gene expression associated with such neurodegenerative diseases.

A. NEBR1-Encoding Nucleic Acids

NEBR1-encoding nucleic acids may be used for a variety of purposes in accordance with the present invention. NEBR1-encoding DNA, RNA, or fragments thereof may be used as probes to detect the presence of and/or expression of genes encoding NEBR1 proteins. Methods in which NEBR1-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR).

The NEBR1-encoding nucleic acids of the invention may also be utilized as probes to identify related genes from other animal species. As is well known in the art, hybridization stringencies may be adjusted to allow hybridization of nucleic acid probes with complementary sequences of varying degrees of homology. Thus, NEBR1-encoding nucleic acids may be used to advantage to identify and characterize other genes of varying degrees of relation to NEBR1, thereby enabling further characterization of the regulation of gene expression in neurodegenerative conditions. Additionally, they may be used to identify genes encoding proteins that interact with NEBR1 (e.g., by the "interaction trap" technique), which should further accelerate identification of the components involved in the control of gene expression during brain injury.

Nucleic acid molecules, or fragments thereof, encoding NEBR1 may also be utilized to control the production of NEBR1, thereby regulating the amount of protein available to participate in the control of gene expression. Alterations in the physiological amount of NEBR1 protein may dramatically affect the activity of other protein factors involved in aberrant gene expression associated with neurodegenerative disorders.

The availability of NEBR1 encoding nucleic acids enables the production of strains of laboratory mice carrying part or all of the NEBR1 gene or mutated sequences thereof. Such mice may provide an in vivo model for assessing the genetic components involved the control of gene expression altered by brain injury. Alternatively, the NEBR1 sequence information provided herein enables the production of knockout mice in which the endogenous gene encoding NEBR1 has been specifically inactivated. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will facilitate the molecular elucidation of the transcription suppressor role of NEBR1.

A transgenic mouse carrying the human NEBR1 gene is generated by geenomic integration of exogenous genomic sequence encoding human NEBR1 or gene targeting of mouse NEBR1 by direct replacement of the mouse NEBR1 gene with that of the human gene. These transgenic animals are useful for drug screening studies as animal models for human diseases and for eventual treatment of disorders or diseases associated with biological activities modulated by NEBR1. A gene-targeted animal carrying a "knock out" of NEBR1 is useful for assessing the role of NEBR1 in controling gene expression.

As a means to define the role that NEBR1 plays in mammalian systems, mice may be generated that cannot make NEBR1 protein because of a targeted mutational disruption of the NEBR1 gene.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene.

The altered NEBR1 gene generally should not fully encode the same NEBR1 protein native to the host animal and its expression product should be altered to a minor or great degree, or absent altogether. However, it is conceivable that a more modestly modified NEBR1 gene will fall within the compass of the present invention if it is a specific alteration.

The DNA used for altering a target gene may be obtained by a wide variety of techniques that include, but are not limited to, isolation from genomic sources, preparation of cDNAs from isolated mRNA templates, direct synthesis, or a combination thereof.

A type of target cell for transgene introduction is the embryonal stem cell (ES). ES cells may be obtained from pre-implantation embryos cultured in vitro (Evans et al., (1981) Nature 292: 154–156; Bradley et al., (1984) Nature 309: 255–258; Gossler et al., (1986) Proc. Natl. Acad. Sci. 83: 9065–9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated NEBR1 genes to selectively inactivate the wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56: 145–147; Bradley et al., (1992) Bio/Technology 10: 534–539).

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$-fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabinofluranosyl)-5-iodouracil, (FIAU). By this counter selection, the number of homologous recombinants in the surviving transformants can be increased.

As used herein, a "targeted gene" or "knock-out" is a DNA sequence introduced into the germline or a non-human animal by way of human intervention, including but not limited to, the methods described herein. The targeted genes of the invention include DNA sequences which are designed to specifically alter cognate endogenous alleles.

Methods of use for the transgenic mice of the invention are also provided herein. Therapeutic agents for the treatment or prevention of neurodegenerative disorders may be screened in studies using NEBR1 transgenic mice.

As described above, NEBR1-encoding nucleic acids are also used to advantage to produce large quantities of substantially pure NEBR1 protein, or selected portions thereof.

B. NEBR1 Protein and Antibodies

Purified NEBR1, or fragments thereof, may be used to produce polyclonal or monoclonal antibodies which also may serve as sensitive detection reagents for the presence and accumulation of NEBR1 (or complexes containing NEBR1) in mammalian cells. Recombinant techniques enable expression of fusion proteins containing part or all of the NEBR1 protein. The full length protein or fragments of the protein may be used to advantage to generate an array of monoclonal antibodies specific for various epitopes of the protein, thereby providing even greater sensitivity for detection of the protein in cells.

Polyclonal or monoclonal antibodies immunologically specific for NEBR1 may be used in a variety of assays designed to detect and quantitate the protein. Such assays include, but are not limited to: (1) flow cytometric analysis; (2) immunochemical localization of NEBR1 in brain cells and other cells infected with HIV; and (3) immunoblot analysis (e.g., dot blot, Western blot) of extracts from various cells. Additionally, as described above, anti-NEBR1 can be used for purification of NEBR1 (e.g., affinity column purification, immunoprecipitation).

From the foregoing discussion, it can be seen that NEBR1-encoding nucleic acids, NEBR1 expressing vectors, NEBR1 proteins and anti-NEBR1 antibodies of the invention can be used to detect NEBR1 gene expression in HIV infected to cells and alter NEBR1 protein accumulation for purposes of assessing the genetic and protein interactions involved in neurodestructive diseases such as HIV.

Exemplary approaches for detecting NEBR1 nucleic acid or polypeptides/proteins include:

a) comparing the sequence of nucleic acid in the sample with the NEBR1 nucleic acid sequence to determine whether the sample from the patient contains mutations; or b) determining the presence, in a sample from a patient, of the polypeptide encoded by the NEBR1 gene and, if present, determining whether the polypeptide is full length, and/or is mutated, and/or is expressed at the normal level; or c) using DNA restriction mapping to compare the restriction pattern produced when a restriction enzyme cuts a sample of nucleic acid from the patient with the restriction pattern obtained from normal NEBR1 gene or from known mutations thereof; or, d) using a specific binding member capable of binding to a NEBR1 nucleic acid sequence (either normal sequence or known mutated sequence), the specific binding member comprising nucleic acid hybridizable with the NEBR1 sequence, or substances comprising an antibody domain with specificity for a native or mutated NEBR1 nucleic acid sequence or the polypeptide encoded by it, the specific binding member being labeled so that binding of the specific binding member to its binding partner is detectable; or, e) using PCR involving one or more primers based on normal or mutated NEBR1 gene sequence to screen for normal or mutant NEBR1 gene in a sample from a patient.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples and they do not need to be listed here. Further, the term "specific binding pair" is also applicable where either or both of the specific binding member and the binding partner comprise a part of a large molecule. In embodiments in which the specific binding pair are nucleic acid sequences, they will be of a length to hybridize to each other under conditions of the assay, preferably greater than 10 nucleotides long, more preferably greater than 15 or 20 nucleotides long.

In most embodiments for screening for alleles associated with the control of gene expression during HIV brain infection and subsequent injury, the NEBR1 nucleic acid in the sample will initially be amplified, e.g. using PCR, to increase the amount of the templates as compared to other sequences present in the sample. This allows the target sequences to be detected with a high degree of sensitivity if they are present in the sample. This initial step may be avoided by using highly sensitive array techniques that are becoming increasingly important in the art.

The identification of the NEBR1 gene and its association with infectious disease and neurodegenerative disorders paves the way for aspects of the present invention to provide the use of materials and methods, such as are disclosed and discussed above, for establishing the contribution of this protein to the control of gene expression during HIV-1 induced brain injury.

Such knowledge should facilitate planning of appropriate therapeutic and/or prophylactic measures, permitting stream-lining of treatment. The approach further streamlines treatment by targeting those patients most likely to benefit.

According to another aspect of the invention, methods of screening agents to identify suitable drugs for inhibiting or augmenting NEBR1 function are provided.

The NEBR1 polypeptide or fragment employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between a NEBR1 polypeptide or fragment and the agent being tested, or examine the degree to which the formation of a complex between a NEBR1 polypeptide or fragment and a known ligand is interfered with by the agent being tested.

Another technique for drug screening provides high throughput screening for compounds having suitable binding affinity to the NEBR1 polypeptides and is described in detail in Geysen, PCT published application WO 84/03564, published on Sep. 13, 1984. Briefly stated, large numbers of different, small peptide test compounds are synthesized on a solid substrate, such as plastic pins or some other surface. The peptide test compounds are reacted with NEBR1 polypeptide and washed. Bound NEBR1 polypeptide is then detected by methods well known in the art.

Purified NEBR1 can be coated directly onto plates for use in the aforementioned drug screening techniques. However, non-neutralizing antibodies to the polypeptide can be used to capture antibodies to immobilize the NEBR1 polypeptide on the solid phase.

This invention also contemplates the use of competitive drug screening assays in which neutralizing antibodies capable of specifically binding the NEBR1 polypeptide compete with a test compound for binding to the NEBR1 polypeptide or fragments thereof. In this manner, the antibodies can be used to detect the presence of any peptide which shares one or more antigenic determinants of the NEBR1 polypeptide.

A further technique for drug screening involves the use of host eukaryotic cell lines or cells (such as described above) which have a nonfunctional NEBR1 gene. These host cell lines or cells are defective at the NEBR1 polypeptide level. The host cell lines or cells are grown in the presence of drug compound. The rate of growth of the host cells is measured to determine if the compound is capable of regulating the growth of NEBR1 defective cells.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9: 19–21. In one approach, one first determines the three-dimensional structure of a protein of interest (e.g., NEBR1 polypeptide) or, for example, of the NEBR1-DNA complex, by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249: 527–533). In addition, peptides (e.g., NEBR1 polypeptide) may be analyzed by an alanine scan (Wells, 1991) Meth. Enzymol. 202: 390–411. In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, one may design drugs which have, e.g., improved NEBR1 polypeptide activity or stability or which act as inhibitors, agonists, antagonists, etc. of NEBR1 polypeptide activity. By virtue of the availability of cloned NEBR1 sequences, sufficient amounts of the NEBR1 polypeptide may be made available to perform such analytical studies as x-ray crystallography. In addition, the knowledge of the NEBR1 protein sequence provided herein will guide those employing computer modeling techniques in place of, or in addition to x-ray crystallography.

III Therapeutics

A. Pharmaceuticals and Peptide Therapies

The NEBR1 polypeptide/proteins, antibodies, peptides and nucleic acids of the invention can be formulated in pharmaceutical compositions. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

B. Methods of Gene Therapy

As a further alternative, the nucleic acid encoding the authentic biologically active NEBR1 polypeptide could be used in a method of gene therapy, to treat a patient who is unable to synthesize the active "normal" polypeptide or unable to synthesize it at the normal level, thereby providing the effect elicited by wild-type NEBR1 and suppressing the occurrence of "abnormal" NEBR1 lacking the ability to perform transcriptional control functions.

Vectors such as viral vectors have been used in the prior art to introduce genes into a wide variety of different target cells. Typically the vectors are exposed to the target cells so that transformation can take place in a sufficient proportion of the cells to provide a useful therapeutic or prophylactic effect from the expression of the desired polypeptide. The transfected nucleic acid may be permanently incorporated into the genome of each of the targeted tumor cells, providing long lasting effect, or alternatively the treatment may have to be repeated periodically.

A variety of vectors, both viral vectors and plasmid vectors are known in the art, see U.S. Pat. No. 5,252,479 and WO 93/07282. In particular, a number of viruses have been used as gene transfer vectors, including papovaviruses, such as SV40, vaccinia virus, adenovirus, herpes viruses including HSV and EBV, and retroviruses. Many gene therapy protocols in the prior art have employed disabled murine retroviruses.

Gene transfer techniques which selectively target the NEBR1 nucleic acid to brain tissues and macrophages are preferred. Examples of this include receptor-mediated gene transfer, in which the nucleic acid is linked to a protein ligand via polylysine, with the ligand being specific for a receptor present on the surface of the target cells.

The following materials and methods are provided to facilitate the practice of the present invention.

Monocyte Culture, HIV-infection and LPS-activation

Human monocytes were obtained from leukophoresis of HIV-1, HIV-2 and hepatitis B seronegative donors and counter current centrifugal elutriation as described previously (Gendelman et al., 1988). Monocytes were seeded at 33 million cells/T-75 culture flask for RNA analyses; 1 million cells/well of a 2-well poly-D-lysine coated Chambertek slides (Beckton Dickinson, Bedford, Mass.) for immunohistochemical analyses; or 3 million cells/well of a 6-well plate for RT analysis. Cells were grown in Dulbecco's Modified Eagles Media (DMEM; Life Technologies supplemented with 10% heat-inactivated pooled human serum, 1% L-glutamine (Gibco BRL), 50 µg/ml gentamicin (Sigma), 10 µg/ml ciprofloxacin (Sigma) and 1000 U/L highly purified recombinant monocyte colony stimulating factor (MCSF; a generous gift from Genetics Institute Inc., Cambridge, Mass.). After seven days of culture, the MDMs were infected at a multiplicity of infection of 0.1 with HIV-1$_{ADA}$ in DMEM without MCSF. Seven days after infection, MDM were activated with lippopolysaccharide (LPS; 1 µg/ml; Sigma) for one hour. All cells (treated and control) were washed briefly with phosphate buffered saline (PBS) and incubated an additional four hours with media for further experiments.

mRNA Differential Display cDNA from human MDM samples (0.25 and 0.75 µg total RNA/tube of control, HIV-1-infected, LPS-activated and HIV-1-infected/LPS-activated) was prepared using single-base anchored oligo-dT antisense primers (RNAimage Kit 1, GenHunter Corp.) according to the manufacturer's protocol. PCR was carried out in duplicate using arbitrary primers (H-AP1–H-AP8) and $^{35}$S-dATP (ICN). The resulting $^{35}$S-labeled polymerase chain reaction (PCR) products were run on 6% denaturing polyacrylamide gels with 6M urea, dried overnight onto Whatman 3MM paper, exposed to storage screens and read on a model 425B PhosphorImager (Molecular Dynamics). Subsequently, the gels were exposed to X0MAT XAR2 film (Kodak) in order to localize and cut out the expressed sequence tags (ESTs).

Cloning the ESTs

Bands were selected for EST cloning if they were up-regulated in experimental groups versus control groups. Bands were isolated from the gel, re-amplified by PCR and subsequently blunt-end cloned into pCR-TRAP (Gen-Hunter). Tetracycline-resistant colonies were checked for inserts by colony PCR and the DNA sequences obtained by using vector specific primers (Lgh and Rgh) according to manufacturer's instructions. The DNA sequences were searched against the non-redundant version of (Genbank+ Gembl) using BLAST and later NETBLAST subroutines. Housekeeping genes such as actin were identified and not examined further. All other ESTs were subjected to the physiological screen.

Physiological Screen of ESTs

EST-specific primer sets were used in reverse transcription (RT)-PCR experiments using total RNA from various regions of diseased (HIV encephalitis and HIV-1 infected without neurological symptoms) and control human brains acquired from the Center for Neurovirology and Neurodegenerative Disorders (CNND) Tissue and Specimen Bank. 0.5 μg of total RNA was mixed with 0.25 μg of antisense primer and reverse transcription was carried out by first incubating at 70° C. for 10 minutes, cooling to 4° C., and then adding of 50 U Superscript I reverse transcriptase with subsequent incubation for 15 minutes at 37° C. and denaturation for 10 minutes at 95° C. For PCR amplification, 0.5 μg sense and an additional 0.25 μg antisense primers were added to the newly transcribed DNA using the following parameters: 2 minutes at 95° C., followed by 28 cycles of 30 seconds at 94° C., 30 seconds at 50° C. and one minute at 72° C. RT-PCR products were analyzed by agarose gel electrophoresis and PCR-amplified ESTs were quantified by Southern blot analysis according to standard protocol using $^{32}$P-labeled EST-specific oligonucleotides as probes. Signals were recorded on storage screens, read on the PhosphorImager and quantitated by ImageQuant software. In parallel, RT-PCR assays were done for β-actin to normalize the signals.

Cloning of NEBR1

A 2438 bp fragment of NEBR1 was obtained by RT-PCR of MDM RNA. Here oligo dT was used for the reverse transcription step followed by the addition of sense and antisense primers which were 5'-GAAAATCCAAACAC-CTATCC-3' and 5'-AAGGACATTTCTGCTTACTC-3', respectively. The thermocycler parameters were 40 cycles of 30 seconds at 95° C., 30 seconds at 50° C. and 3 minutes at 72° C. The ends of this fragment were filled in using T4 DNA polymerase (Life Technologies) and cloned into the pCR-TRAP vector (GenHunter). The NEBR1 full-length gene was also cloned into the pCDNA3.1+ vector to be used in subsequent transfection studies.

RT-PCR Analyses on Cultured MDM

To verify up-regulation in HIV-infected MDM, we performed RT-PCR on RNA obtained from monocytes from 7 different donors. The RNA samples were from MDM that was +/− HIV-1-infection and/or LPS activated as described previously. Briefly, 0.5 μg of total RNA was reverse transcribed using 0.25 μg of the antisense primer (5'-GGCT-GTCTTCCAATAAAAC-3') and Superscript RT. The resultant DNA was amplified with the antisense primer (0.25 μg) and 0.5 μg of the sense primer (5'-GTGAGCCTCTCCAT-AATTAG-3') as described in the Physiological Screen for ESTs.

Northern Analysis of NEBR1 Gene

The tissue distribution of NEBR1 mRNA was examined by Northern blotting using MTN Blots (Human MTN Blot and Human Brain MTN Blot II; Clontech). DNA radioprobe was generated from NEBR1 gene using [α-$^{32}$P]-dCTP, random hexamer and Klenow fragment. The membranes were hybridized to the radioprobe using ExpressHyb Hybridization Solution (Clontech), washed, and exposed to Phosphor Screen. The radioactive signals were visualized and quantified using a PhosphorImager. The membranes were stripped for radioprobes and re-hybridized with β-actin radioprobe for the normalization of NEBR1 mRNA signal with β-actin mRNA signal.

NEBR1 Adenoviral Constructs.

Recombinant adenoviruses were constructed. Full-length NEBR1 cDNA was subcloned into a mammalian expression vector. The plasmid was linearized by restriction digestion and subcloned into adenoviral backbone DNA by homologous recombination in *E. coli* (BJ5183). The recombinant DNA was purified by maxiprep, linearized by restriction digestion, and transfected into HEK293 cells using Lipofectamine Plus (Life Technologies). The viruses were harvested from the media and amplified by repeated infection into HEK293 cells, followed by purification using CsCl banding. The purified virus was used as $3\times10^7$ expression-forming units (efu)/ml for infecting $3\times10^6$ MDM in 6-well plates and $2\times10^6$ efu/ml for $1\times10^5$ MDM in 24-well plates. The infection was done for 1 hour at 37° C., the media replaced with fresh complete media, and incubated for 48 hours. The expression of the NEBR1 insert was determined by performing RT-PCR on RNA extracted from adenoviral infected MDM with and without the NEBR1 insert.

GAL4 Assay to Determine Activation/Suppression Activity

GAL4 DNA binding domain-NEBR1 (GBD-NEBR1) was constructed by subcloning the full-length NEBR1 gene into pFA-CMV vector using BamH I-Xho I sites. GAL4-luciferase reporter gene (GAL4-Luc, 0.3 μg), thymidine kinase promoter-driven *Renilla* luciferase gene (pTK-RL, 0.1 μg), and GBD-NEBR1 (0.6 μg) were transfected in HEK293 cells ($1\times10^6$ cells/well) by lipofection method (6 μl Lipofectamine) in 1.5 ml complete DMEM media. Forty-eight hours after transfection, cells were collected and the luciferase activity measured by luminometer using Dual-Luciferase kit (Promega). UAS-TK-LUC, which contains GAL4-tk promoter-luciferase gene (kindly provided from Dr. Bill Lowe at Northwestern University), was utilized instead of GAL4-Luc for monitoring transcriptional suppressor activity. The GBD-NEBR1 mutants that were generated were 1–58, 1–115, 1–241, 1–300 and 1–711. KRAB Box A (27–66) and KRAB Box B (67–89) were removed from the original amino acid sequence for generating GBD-NEBR1. All deletion mutants of GBD-NEBR1 (1–58, 1–115, 1–241, 1–300, and 1–711, ΔBox A, Δbox AB, Box A, Box B, Box AB) were constructed by the usage of unique restriction sites and PCR.

cDNA Microarrays

Human Cytokine Expression Array (R&D systems) was utilized for cDNA microarrays. Total RNA was extracted from human MDM (n=3) infected with recombinant adenoviral constructs with and without the NEBR1 insert. Probe cDNA was prepared from 10 μg of total RNA utilizing the Human Cytokine-specific primers (R & D systems) and

[α-$^{32}$P]-dCTP (Amersham). Pre-hybridization and hybridization were carried out using ExpressHyb solution (Clontech) according to manufacturer's instructions. Hybridization was carried out by adding 2×10$^6$ cpm of probe/ml of ExpressHyb solution at 65° C. overnight. The radioactive membranes were washed and exposed to a Phosphor Screen. Band intensities were quantified using PhosphoImager and ImageQuant software.

Reverse Transcriptase (RT) Analysis

Supernatants were collected from days 3, 5, 7 and 10 post-HIV-1-infection from human MDM (n=4) that had previously been infected with recombinant adenoviral constructs with and without the NEBR1 insert (CMV, CMV-NEBR1 or no virus). The supernatants were subjected to RT analysis by following standard protocol (Vincenzi et al., 1999, supra). At day 10 post-HIV-1-infection, total DNA was extracted by the TRIzol method and stored at −80° C. for future analyses.

HIV-Tat/HIV-LTR Transreporting System

HEK 293 cells (0.5 million cells per 12-well plates) were transfected with pCDNA3-NEBR1 (0.7 µg), pCDNA3 (0.7 µg), pTK-RL (0.1 µg), pSV2-Tat (0.1 µg) and LTR-Luc (0.7 µg) using 10 µl Gene Porter (Gene Therapy System). Twenty-four hours after transfection, cells were lysed and subjected to dual-luciferase assay (Promega) using luminometer (Berthold LB96V).

NEBR1 Polyclonal Antibody Production

Synthetic NEBR1 peptide (SQKPQVLGPEKQDGS) from the N-terminus of the protein sequence was synthesized by Research Genetics and rabbits immunized for raising antisera (Covance Research Products). All resulting bleeds and purified antibody were tested for NEBR1 specificity by in vitro transcription of NEBR1 protein from pCDNA3.1+ constructs using $^{35}$S and the PROTEINIIscript kit (Ambion) for the T7 promoter.

Immunoprecipitation and PAGE analysis of NeBR1 Immune Complexes

Protein was transcribed and translated, in vitro, with $^{35}$S from vectors with or without NEBR1 insert. The resulting complexes were incubated overnight with or without NEBR1 polyclonal antibody. Ten micrograms of protein was loaded per well and run on a 4% stacking and 10% separating polyacrylamide gel against pre-stained broad range markers. The gel was dried onto Whatman paper, exposed to a phosphoimaging screen for 72 hours and subsequently analyzed on the phosphoimager.

Immunohistochemical Analyses

Immunohistochemical analysis was initially performed on MDM cultured on 2-well Chambertek Slides slides and subsequently performed on paraffin-fixed brain tissue from HIVE cases obtained from Dr. Susan Morgello of the Manhattan HIV Brain Bank (MHBB) and control cases obtained from the CNND Brain Bank. Immunohistochemistry was performed on approximately 5 µm paraformaldehyde-fixed, paraffin embedded sections of brain tissue from the frontal cortex. Human MDM were identified immunocytochemically with antiCD68 KP-1 (1:100, Dako) monoclonal antibody (mAb). Viral gene products were identified by using a 1:10 dilution of HIV-1 p24 antigen (mAb, Dako). To detect NEBR1 positive cells, the human polyclonal antibody made against this antigen was used at a 1:100 dilution. To detect the CD68, p24 and NEBR1 antigens on paraffin sections, avidin-biotin immunoperoxidase staining with ABC kit (Vectastain Elite, Vector) was used with 3,3'-diaminobenzidine (Vector) as the chromagen. All sections were counter-stained with Hemotoxylin.

The following examples are provided to illustrate certain embodiments of the invention. They are not intended to limit the invention in any way.

EXAMPLE I

Cloning and Characterization of NEBR1 mRNA Differential Display and the Discovery of NEBR1

We compared control (uninfected/unactivated), LPS-activated, HIV-1 infected, and HIV-1 infected and LPS-activated MDM. Utilizing the mRNA differential display technique, one of the genes isolated was shown to be up-regulated in the HIV-1 infected and HIV-1 infected LPS-stimulated MDM. This gene (also known as OTK18 or Zinc Finger Protein 175 (ZNF 175), had previously been submitted to GenBank as a result of random determination of sequences from a commercially available cDNA library (Saito et al., 1996) and was shown to be composed of 711 amino acids and localized at chromosome 19q13.4. We have elected to call this novel gene Nebraska1 (NEBR1). Its entire 17 kb genomic sequence was recently deposited in GenBank (accession number AC018755 and AC020914), which is composed of 6 exons and 6 introns, generating 4 segments of coding sequences (FIG. 1).

NEBR1 Gene Expression is Up-regulated in HIV-infected MDM and Brain Tissue and Ubiquitously Expressed in Uninfected Human Tissues To confirm whether HIV-1 infection of human MDM results in up-regulation of NEBR1 expression, we did a series of RT-PCR analyses on total RNA obtained from human MDM which were either infected or uninfected and with and without LPS activation. We performed RT-PCR on monocytes from 7 different donors. For all but two of these samples (donor #1 and #5), the cells were subjected to all treatment conditions before analysis (Table 1). These results show that in five out of the seven donors tested (all but donors #5 and #7), there was a statistical up-regulation of NEBR1 gene expression in HIV-infected MDM as compared to uninfected/unactivated MDM, thus supporting our hypothesis. Chi square analysis of this data demonstrate independence of assortment (chi square=0.047619048; P-value=0.59338371) based on a 3:1 ratio with degrees of freedom=1. Interestingly, when MDM were both HIV-infected and LPS-activated, there was only one instance (donor #7) in which there was a significant up-regulation of NEBR1 gene expression, which was seen in this treatment group as compared to HIV-infected MDM alone. This trend was also apparent in LPS-activated treatments as compared to HIV-infected MDM.

TABLE 1

NEBR1/β-actin RT-PCR Ratios

Statistical comparison n = 3 for each treatment group

| Donor | M vs. L | M vs. H | M vs. HL | L vs. H | L vs. HL | H vs. HL |
|---|---|---|---|---|---|---|
| 1 | 0.04894 | 0.03325[b] | NT | 0.02562[d] | NT | NT |
| 2 | 0.0079 | 0.0000002[b] | 0.01433 | 0.00040[d] | 0.03896 | 0.00219 |
| 3 | 0.00096[a] | 0.00063[b] | 0.00126[e] | 0.00371[d] | 0.00387 | 0.42662 |
| 4 | 0.11301 | 0.00137[b] | 0.44689 | 0.00371[d] | 0.10523 | 0.00161 |
| 5 | 0.00016 | 0.00231 | NT | 0.00495[d] | NT | NT |
| 6 | 0.00096[a] | 0.00063[b] | 0.00126[e] | 0.00371 | 0.00387 | 0.42662 |
| 7 | 0.36854 | 0.16494 | 0.29511 | 0.16961 | 0.13211 | 0.03015[f] |

All reactions for each treatment group were performed in triplicate and the resulting NEBR1 values were normalized to β-actin values.
M, Uninfected/unactivated macrophage RNA used as control RNA
L, LPS activated macrophage RNA
H, HIV-1 infected macrophage RNA
HL, HIV-1 infected/LPS activated macrophage RNA
NT, not tested
[a]NEBR1/actin ratio is statistically upregulated in LPS-activated RNA samples as compared to MDM controls.
[b]NEBR1/actin ratio is statistically upregulated in HIV-infected RNA samples as compared to MDM controls.
[c]NEBR1/actin ratio is statistically upregulated in HIV-infected/LPS-activated RNA samples as compared to MDM controls.
[d]NEBR1/actin ratio is statistically upregulated in HIV-infected RNA samples as compared to LPS-activated RNA samples.
[e]NEBR1/actin ratio is statistically upregulated in HIV-infected/LPS-activated RNA samples as compared to LPS-activated RNA samples.
[f]NEBR1/actin ratio is statistically upregulated in HIV-infected/LPS-activated RNA samples as compared to HIV-infected RNA samples.

Figure 2:
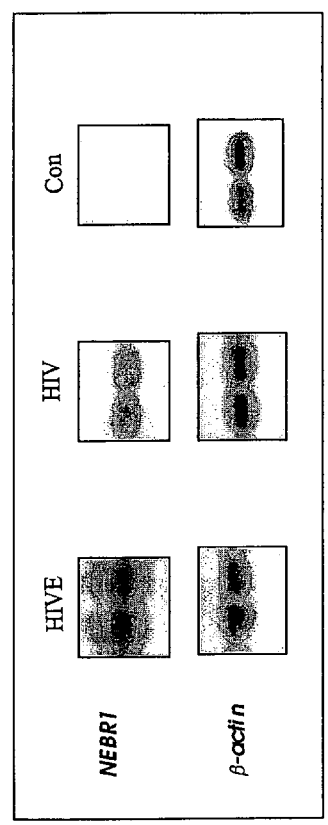
FIG. 2 is a blot showing NEBR1 RNA Expression in Human Brain Tissues from the frontal cortex as analyzed by RT-PCR. Total RNA was collected from HIVE brains, HIV-1 seropositive brains without neurological abnormalities, and control brains (HIV-1 seronegative without neurological disease), and evaluated for NEBR1 and β-actin RNA expression by RT-PCR. 0.5 µg of total RNA was used for each sample, regardless of brain type, and a total of 0.5 µg of sense and anti-sense primers were used to carry out the RT-PCR reaction. As indicated in the figure, up-regulation of NEBR1 gene expression was observed in both HIVE brains (17.1±0.96 OD) and in the HIV-1-seropositive brains without apparent neurological disease (3.4±0.47 OD) when compared to controls (0.33±0.02 OD).

To substantiate these results, we performed physiological screens of NEBR1 gene expression in pathological material utilizing RT-PCR methods. Total RNA was collected from multiple regions of HIVE, HIV-1 seropositive brain(s) without neurological symptoms and control brain tissue without neuropathology. Samples were taken from the frontal cortex, basal ganglia, and cerebellum and subjected to RT-PCR. In frontal cortex, we observed robust expression of NEBR1 compared to β-actin in both HIVE and HIV-1 seropositive without neurological disease samples. See FIG. 2. We also noticed that there were basal levels of NEBR1 expression in control brain tissue, demonstrating that this is not a gene that is simply turned on or off, but that HIV infection and subsequent encephalitis could markedly up-regulate NEBR1 gene expression in human brains. Thus, this data provides in vivo evidence for the up-regulation of NEBR1 gene expression.

Figures 3A, 3B:
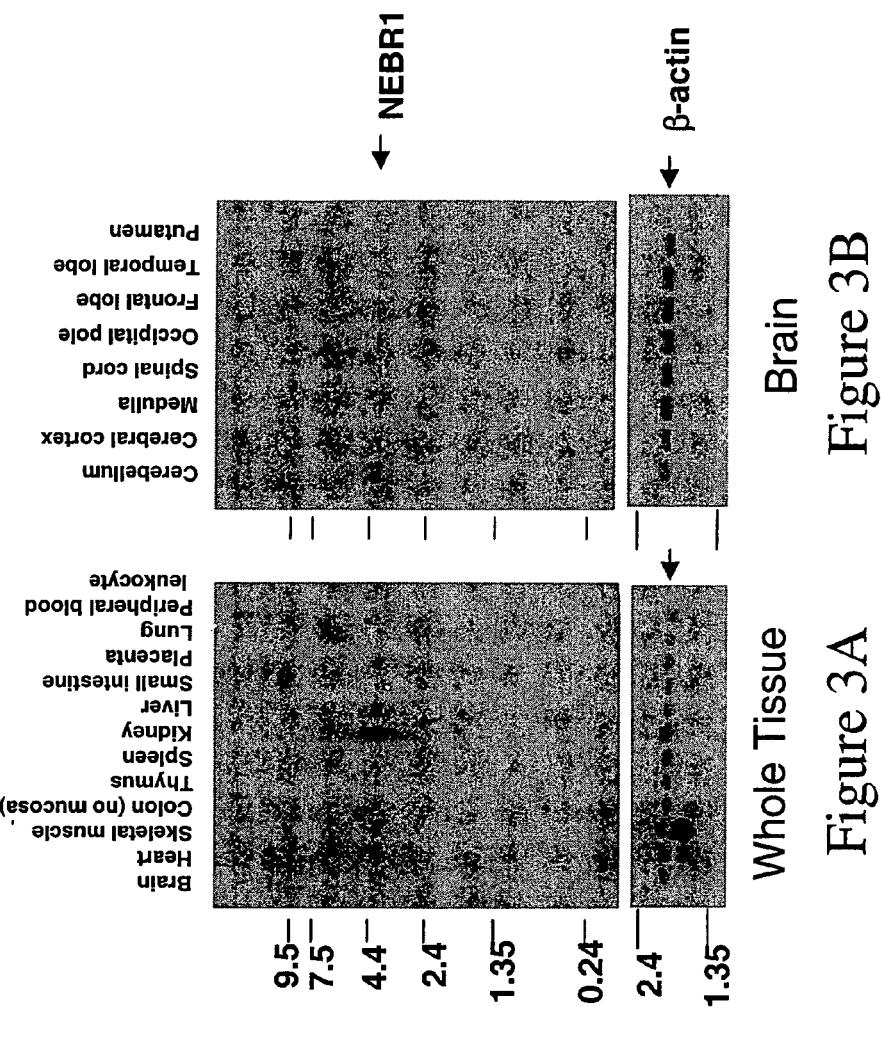
FIGS. 3A, 3B and 3C show the results of Northern Blot Analysis and Quantification of NEBR1 Signal Expression. Northern Blot analysis was performed by using commercially available Northern blot membranes obtained from Clontech. Radioactively labeled NEBR1 was used to probe the blot. The panel on the left (FIG. 3A.) depicts the NEBR1 expression in whole tissue, while the panel on the right (FIG. 3B) depicts expression in specific brain regions. To detect β-actin, the blots were stripped and re-probed with a radioactively labeled β-actin probe. Quantification of NEBR1 signal from the Northern Blots was done by normalizing values for NEBR1 to β-actin values (FIG. 3C).
Figure 3C:
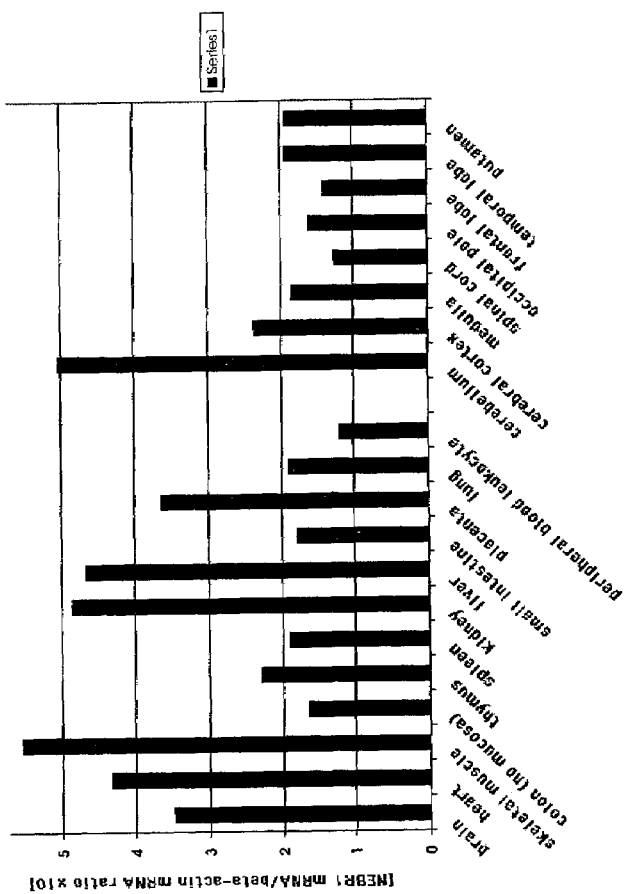

Based upon the finding that NEBR1 was up-regulated in HIV-infected human brain tissue, we performed Northern blot analysis on normal (HIV-1 seronegative) whole tissue and specific brain tissue regions. Northern blot analysis revealed a relatively ubiquitous expression pattern in all tissues with a band migrating at approximately 4.4 kb (FIG. 3A). Quantification of the NEBR1 signal as normalized to β-actin signal values demonstrated high levels of expression in most whole tissues, except peripheral blood lymphocytes (PBL). Also, NEBR1 gene expression was markedly upregulated in the cerebellum as compared to other brain regions (FIG. 3B). FIG. 3C is a graph showing quantitation of the signals depicted in FIGS. 3A and 3B.

NEBR1 is a Transcription Suppressor

Figure 4B:
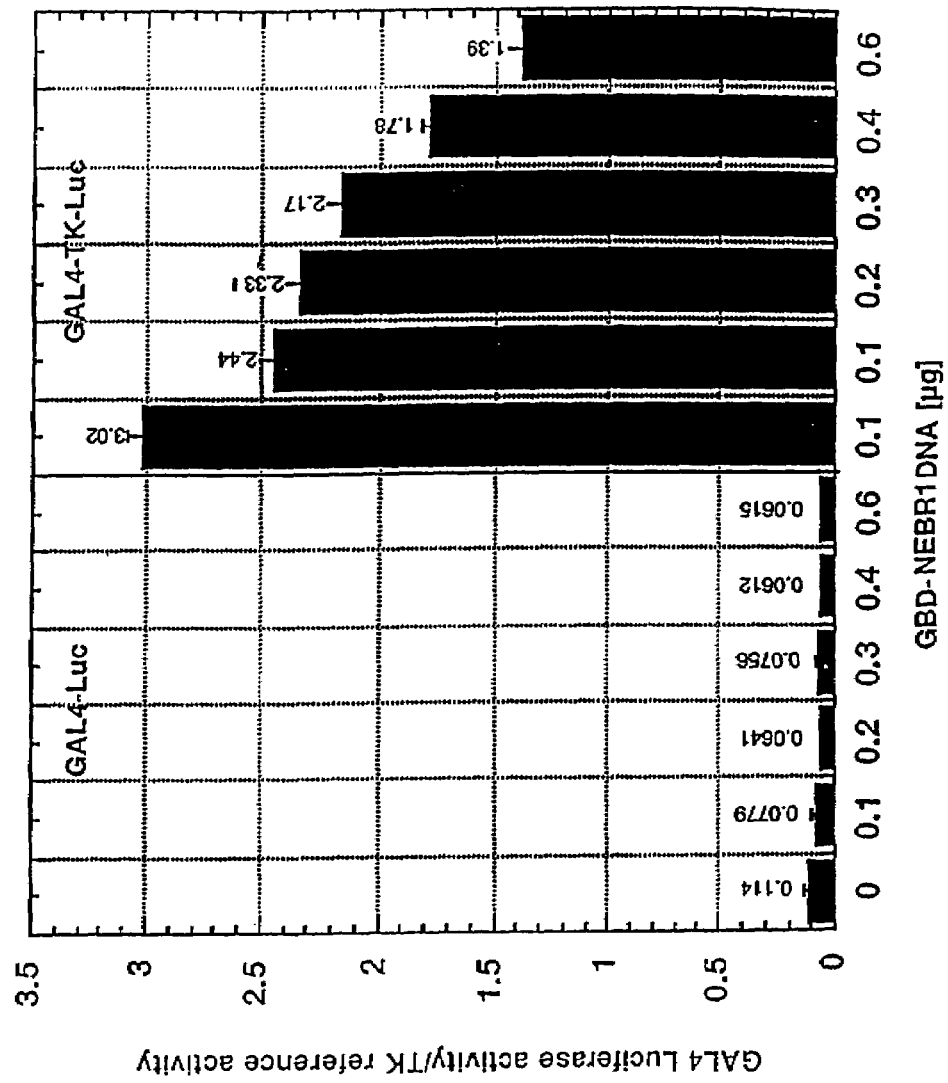

To determine the transcriptional activity of NEBR1, we determined the effect of recombinant GAL4 DNA binding domain-NEBR1 fusion protein (GBD-NEBR1) on GAL4-luciferase and GAL4-thymidine kinase minimal promoter-luciferase reporter gene (GAL4-TK-Luc) transcription in HEK293 cells. A schematic diagram of the constructs utilized for this analysis is provided in FIG. 4A. At 24 hours post transfection into HEK293 cells, GBD-NEBR1 did not activate GAL4-Luc gene transcription, but suppressed GAL4-TK-Luc gene transcription in a DNA dose-dependent manner for up to 54% (FIG. 4B).

Based on these results, we next generated several truncation mutants of GBD-NEBR1 as shown in FIG. 4C, to determine which region of the NEBR1 sequence was responsible for the suppressive function. It was found that mutant 1–58 did not suppress GAL4-TK-Luc gene transcription. However, mutants 1–115, 1–241 and 1–300 suppressed gene transcription equal to full-length 1–711 constructs. Therefore, these data indicate that amino acids 58–115 are responsible for the suppressive function of NEBR1 (FIG. 4D).

Figure 5C:
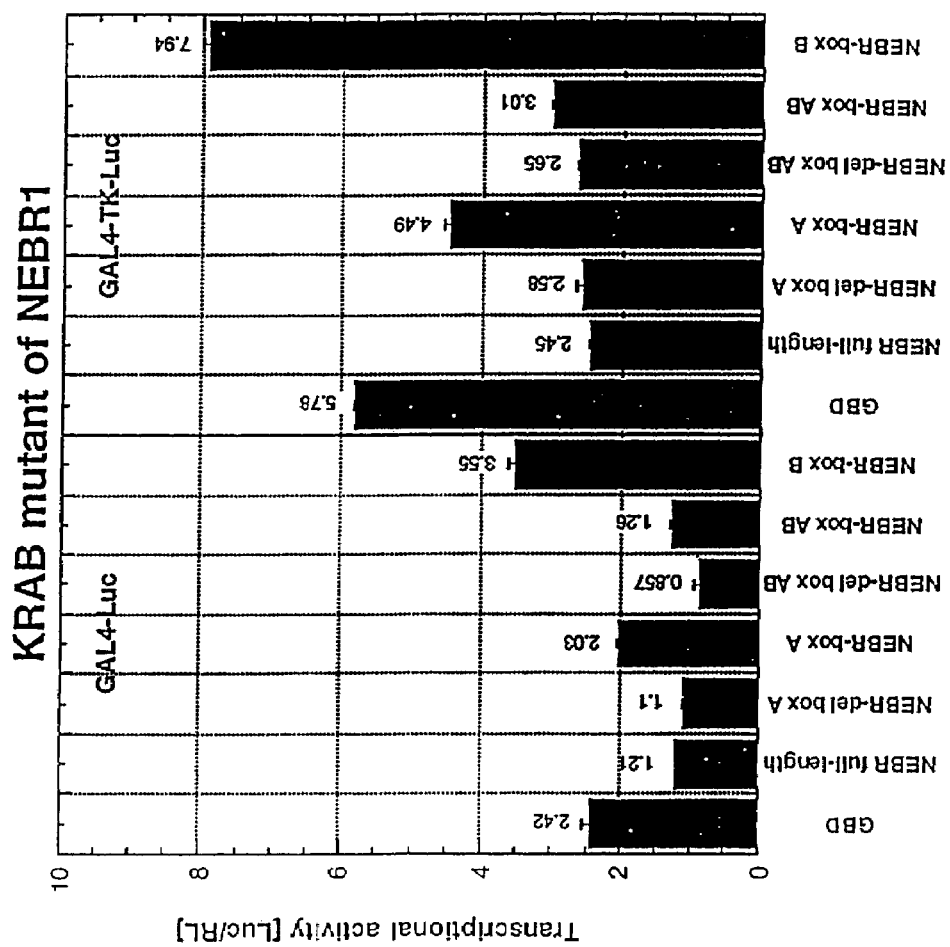
Figure 5D:
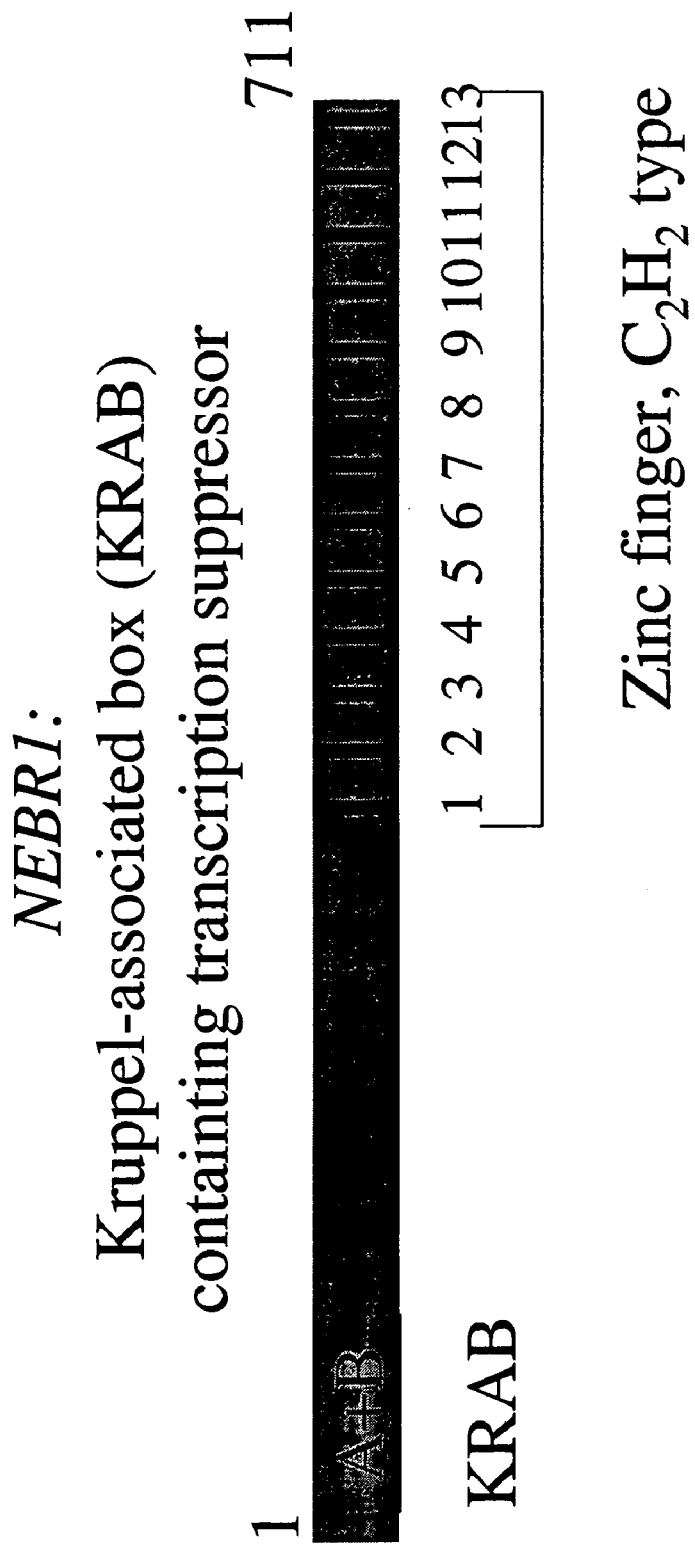
FIG. 5D shows the spatial relationship between the KRAB box doman and the 13 zinc fingers in NEBR1.

The amino acids corresponding to 58–115 were subjected to BLAST subroutines to search for similar amino acid sequences in other mammalian cDNAs. Several zinc-finger proteins (HSZNF41, KID1A, ZNF157, GIOT-3, RBAK and KS1) were found to contain sequences similar to NEBR1. These proteins all share Krüppel-Associated Box (KRAB) motif, which is important for suppression of gene transcription and found in 30% of all known zinc-finger proteins. See FIG. 5A. The closest family member of NEBR1 is HSZNF41, in which there is an extension of KRAB Box B (Box B1) in this family. To determine the effect of KRAB on luciferase activity, we constructed KRAB mutations in NEBR1 as shown in FIG. 5B. The luciferase assay demonstrated that neither GBD alone or GBD-Box B suppressed GAL4-TK-Luc gene transcription. However, GBD-Box A partially suppressed gene transcription, but the other mutants (ΔBox A, ΔBox B and ΔBox AB) suppressed transcription equally as well as full-length NEBR1. See FIG. 5C. These data indicate that expression of Box AB itself is sufficient for the gene suppression activity, but neither Box A or Box B alone are fully functional. The suppressive effect of Box AB suggests the existence of at least one additional transcription suppressive region between KRAB and the 13 zinc-fingers in NEBR1 (FIG. 5D).

NEBR1 Inhibits Migration of MDM in Hippocampal Slices.

The organotypic hippocampal slice culture method was utilized in these assays as previously described (Stoppini 1991). The hippocampi were dissected into 400 μm-thickness transverse slices and cultured on porous (0.4 μm) membrane units (Millicell-CM, Millipore) for 4 days. The brain slices were pre-stained with DiIC18 at 75 μg/ml for 48 hrs before co-culturing. MDM were cultured in media A for 4 days and infected with adenoviruses (R-CMV or R-NEBR1) one day before co-culturing. The DiIC stained brain slices and infected MDM ($5 \times 10^5$ cells per slice) were co-cultured as previously described (Nygaard 1998) for 24 hr. The organotypic slices were washed and analyzed by an laser confocal scanning microscope (LSM410, Zeiss). For detection of the DiIC and GFP signal, FITC and Texas Red filter optics were used. To determine to what extent NEBR1 expression affects infiltration of MDM into the organotypic slice cultures, optical Z-sectioning was performed every 4 μm. The average distance of migration was 150 μm for control MDM, in contrast to 75 μm for NEBR1 expressing MDM. The data indicate that NEBR1 showing the 50% inhibition of MDM migration in the hippocampal slices.

TABLE 2

Migration analysis of MDM in rat hippocampal slices.

|  | Migrated Depth [μm] | Cell Number/ Section of Deepest Migration | Average Distance Migrated [μm] |
| --- | --- | --- | --- |
| R-CMV | 268 | 33 | 150 |
| R-NEBR1 | 220 | 2 | 75 |

NEBR1 Down-regulates HIV-1 Receptor and Co-receptor Expression

To determine which genes are differentially expressed as a result of MDM treatment with large amounts of NEBR1, we constructed recombinant adenoviruses expressing human NEBR1. Human MDM were infected with the recombinant viruses, stimulated with CD40 ligand, and subjected for total RNA extraction. Total RNA was subjected for human cytokine Arrays using cytokine-specific primers (R&D Systems). The cDNA Array covers 375 different cDNA PCR products and their controls of genes important for immune system, cell growth, differentiation, cell adhesion, and metabolism. Interestingly, we found that many genes were down-regulated when recombinant NEBR1 was introduced as compared to controls. Of these genes, we find the down-regulation of the chemokine receptors most interesting (Table 3). We found that CXCR4 CCR-5, and CD4, which have major roles in HIV-1 entry, were all down-regulated in NEBR1 expressing MDM.

TABLE 3

Microarray Table

| Gene Name | Gene Group | Fold Suppression by R-CMV-NEBR1 Adenoviral RNA |
| --- | --- | --- |
| CD14 | Cell Surface Protein | 19.3 |
| CD6 | Cell Surface Protein | 16.6 |

TABLE 3-continued

Microarray Table

| Gene Name | Gene Group | Fold Suppression by R-CMV-NEBR1 Adenoviral RNA |
| --- | --- | --- |
| CD4 | Cell Surface Protein | 11.1 |
| CD38 | Cell Surface Protein | 6.5 |
| CD34 | Cell Surface Protein | 6.4 |
| CXCR-5 | Chemokine Receptor | 9.8 |
| CXCR-4 | Chemokine Receptor | 8.6 |
| CCR-1 | Chemokine Receptor | 6.4 |
| CCR-7 | Chemokine Receptor | 5.6 |
| CCR-9 | Chemokine Receptor | 5.4 |
| CCR-5 | Chemokine Receptor | 3.1 |
| CXCR-1 | Chemokine Receptor | 3.0 |

NEBR1 Suppress HIV-1 Viral Infection

Based upon the results obtained from the cDNA microarray, we decided to test whether increased expression of NEBR1 could affect HIV-1 viral replication in human MDM. To test this hypothesis, we used purified virus either with or without full-length NEBR1 to infect human MDM followed by infection with HIV-1. Media samples were collected at days 3, 5, 7 and 10 post-HIV-1-infection and subjected to HIV reverse transcriptase (RT) assay. We have found that R-NEBR1-CMV suppresses HIV-1 viral replication in human MDM as compared to adenovirus without insert or no adenovirus infection.

Figure 6A:
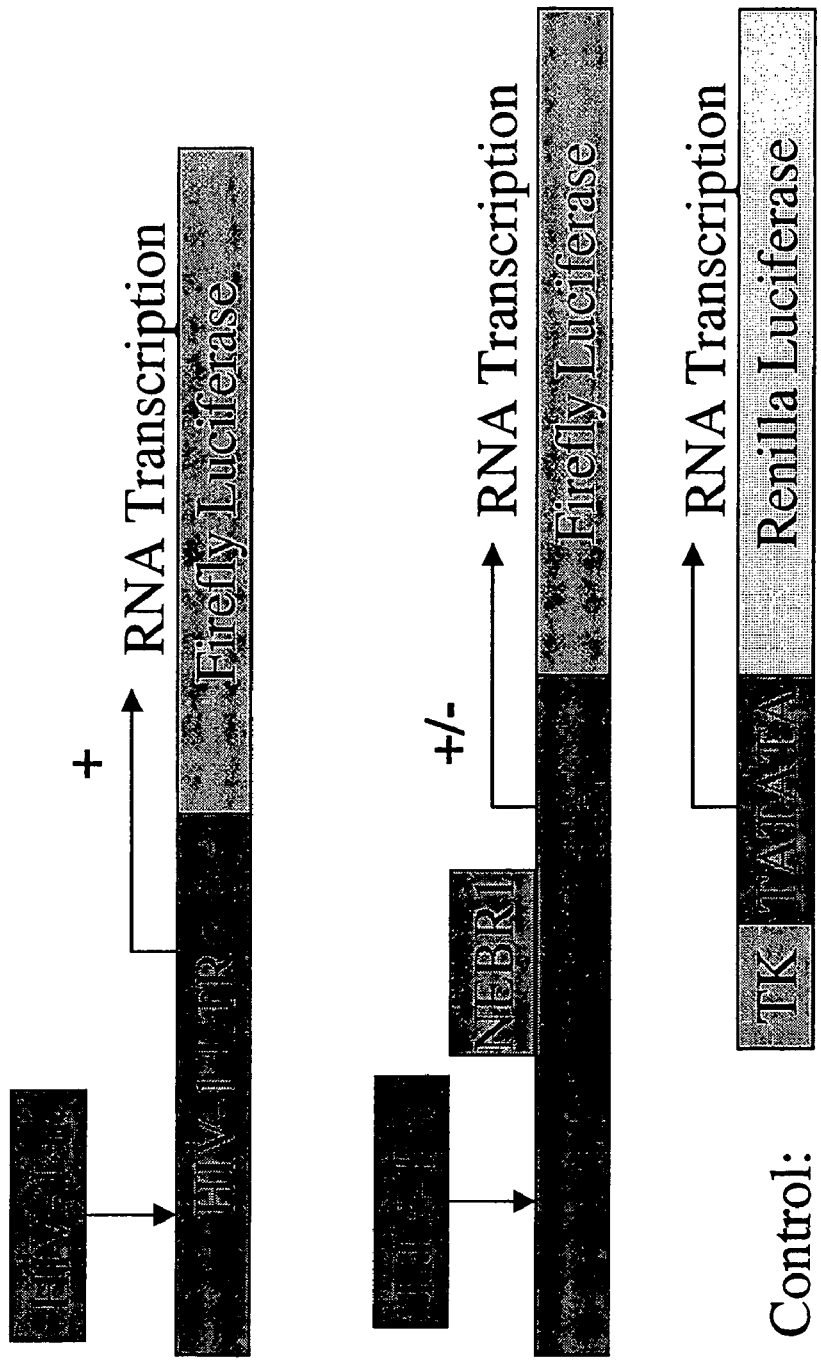
FIGS. 6A and 6B show that NEBR1 suppress HIV-Tat induced HIV-LTR promoter activation.
Figure 6B:
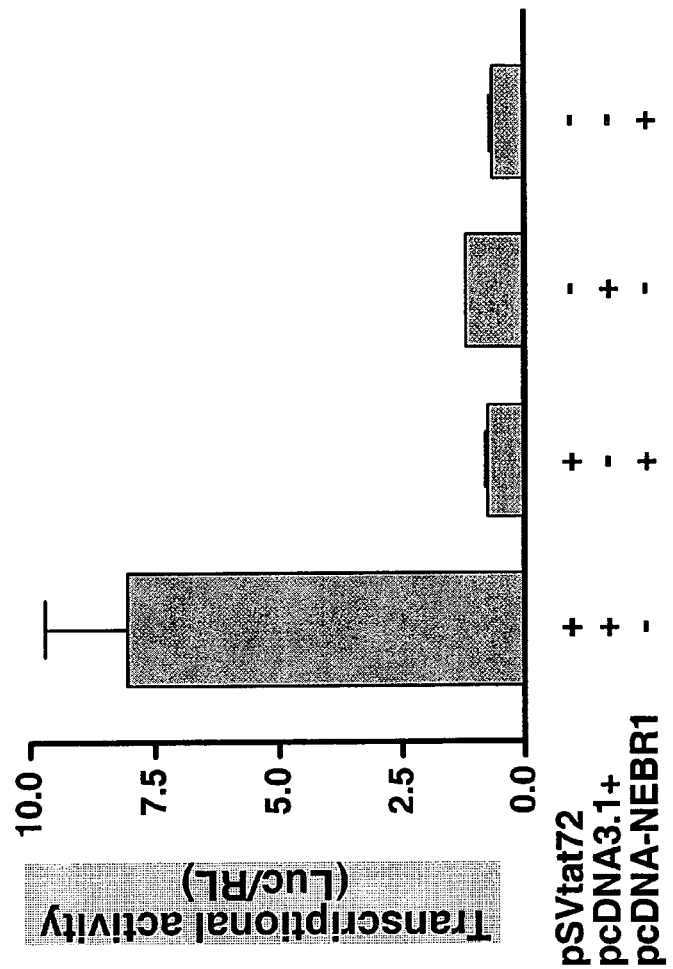

To determine whether NEBR1 binds to regions on the HIV-1 genome, an HIV-Tat/HIV-LTR transreporting system was utilized to analyze the effect of NEBR1 expressing on the HIV-LTR promoter region. See FIG. 6A. The data reveal that NEBR1 suppress HIV-Tat induced HIV-LTR promoter activation. HEK 293 cells were transfected with pCDNA3-NEBR1 (0.7 μg), pCDNA3 (0.7 μg), pTK-RL (0.1 μg), pSV2-Tat (0.1 μg) and LTR-Luc (0.1 μg) using Gene Porter (Gene Therapy System). Twenty-four hours after transfection, cells were lysed and subjected to dual-luciferase assay. PSV2-Tat activated LTR-Luc gene transcription, but was suppressed by the co-transfection of pCDNA-NEBR1 for up to 80%. Control plasmid (pCDNA3) had no effect on LTR-Luc activity with or without co-transfection of pSV2-Tat (FIG. 6B). These data indicate that NEBR1 binds to the HIV-LTR to suppress basal and HIV-Tat mediated RNA transcription, thus exerting its antiretroviral activity in HIV-1 infected cells.

NEBR1 Expression as a Pathological Marker for Disease During HIV-1 Encephalitis

Figure 7:
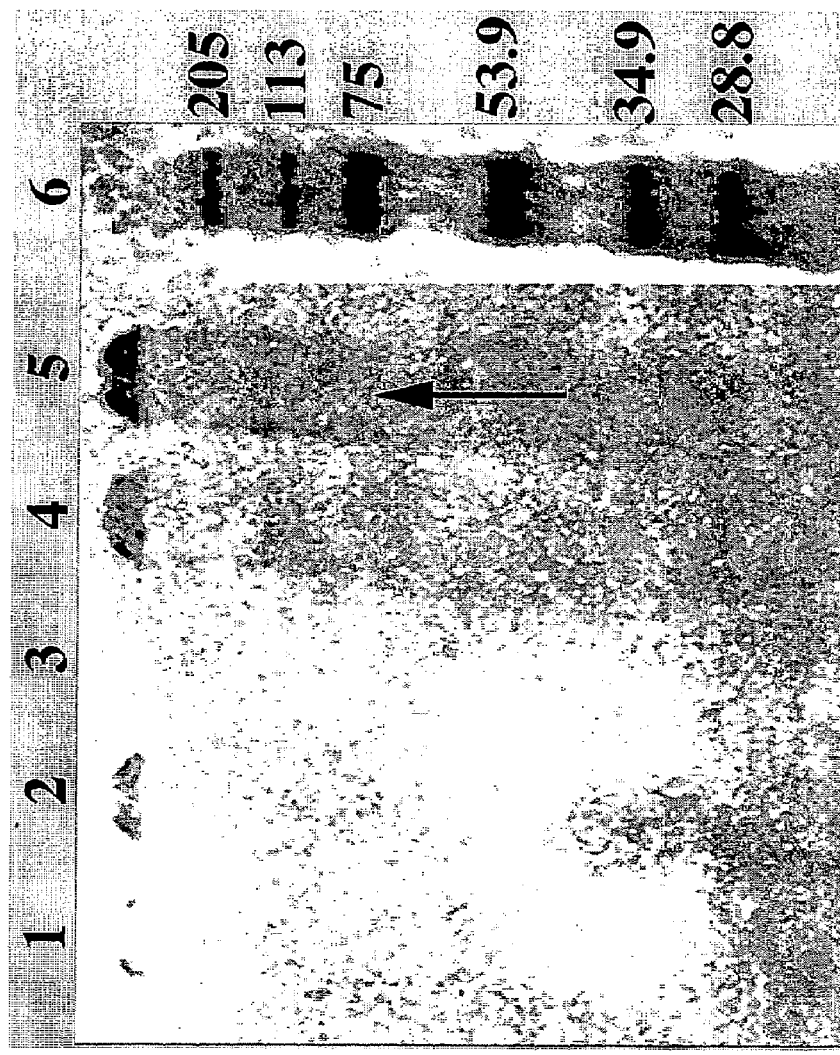
FIG. 7 shows the results from immunoprecipitation and PAGE Analysis of NEBR1 Immune Complexes. Lanes 1, 2, 9 and 10 are empty. Lanes 3 and 6 are broad range markers. Lane 4 is vector+insert with NEBR1 pAb, Lane 5 is vector+insert without NEBR1 pAb, Lane 7 is blank vector with NEBR1 pAb and Lane 8 is blank vector without NEBR1 pAb. The arrow depicts a band migrating at 78 kD, which is the expected size for NEBR1.

Rabbits were immunized with synthetic N-terminus NEBR1 peptide to generate polyclonal anti-NEBR1 antibody. Antibody specificity was confirmed after exposure to primary human MDM transfected with adenoviral vectors containing a full-length NEBR1 insert. Transfected MDMs showed vigorous transfection as demonstrated by visualization of the Green Fluorescent Protein (GFP) tag. Antibody specificity was further confirmed by in vitro translation, immunoprecipitation and PAGE analysis (FIG. 7). Immunoprecipitation and subsequent PAGE demonstrated that polyclonal anti-NEBR1 reacted specifically with the protein that was in vitro transcribed and translated from the plasmid containing the NEBR1 insert and not the empty vector. This is apparent by the intense band that appears on the gel at 78 Kd, which correlates with the predicted size of NEBR1 protein.

Figure 8:
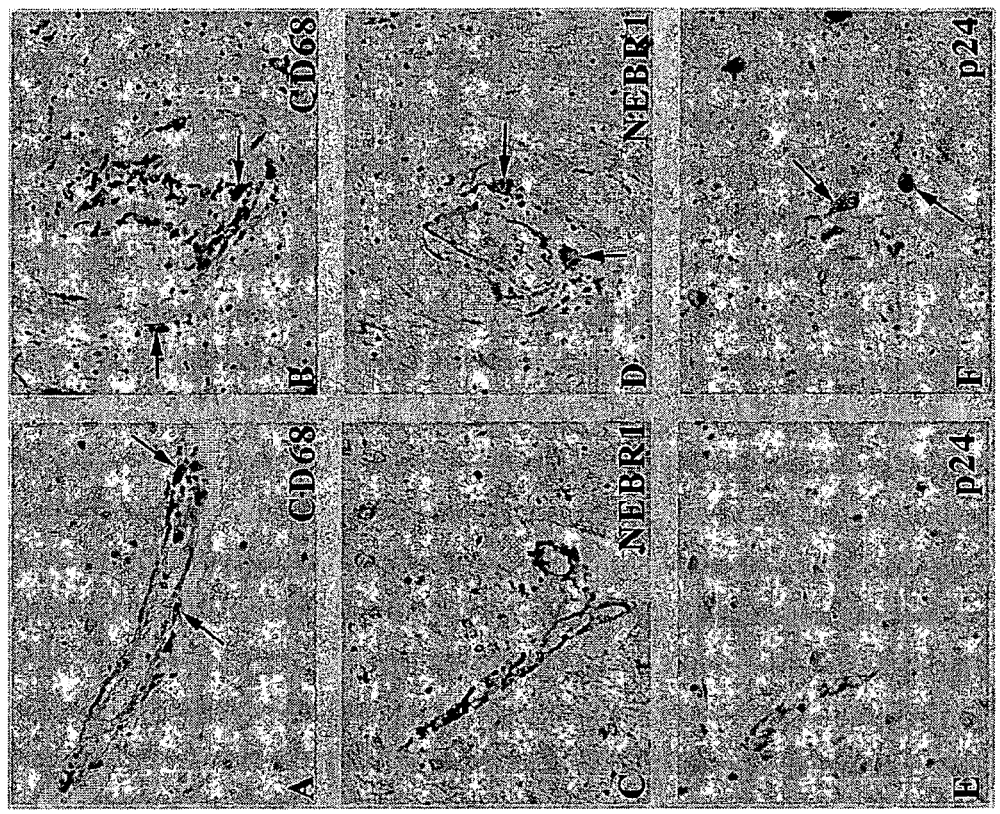
FIGS. 8A–8F are a series of micrographs showing the results from immunohistochemical analysis of NEBR1 Protein in Human MDMs and HIVE Brain Tissue. (A, C and E) These panels represent control (HIV-1 negative) cases of paraffin-embedded brain tissue from the frontal cortex. All panel maginifcations are to 40X. Panel A demonstrates the presence of CD68 positive MDM in the vessel, which are indicated by the arrows. Negative staining for both NEBR1 and p24 is depicted in Panels C and E, respectively. (B, D and F) These panels represent HIVE cases of paraffin-embedded brain tissue from the frontal cortex. All panel magnifications are at 40X. Panel B depicts the influx of CD68 positive MDM, which are depicted by the arrows. The presence of NEBR1 and p24 positive multinucleated giant cells is depicted in Panels D and F, respectively.

A 1:100 dilution of the NEBR1 antibody was used in immunocytochemical analysis of HIVE and HIV-1 seronegative paraffin-embedded brain tissue. Serial sections from the frontal cortex of each of the cases were used for detection of human MDMs by anti-CD68, HIV-1 infection by anti-p24 and cellular localization of NEBR1 by using the anti-NEBR1 antibody (FIG. 8). Panels 8A, 8C and 8E represent HIV-1 seronegative serial sections of frontal cortex, while panels 8B, 8D and 8F represent HIVE serial sections of frontal cortex. Panels 8A and 8B demonstrate large areas of positive (brown) cells concentrated around vessels. In panel 8B, a portion of these cells are mulitnucleated giant cells, which are a neuropathological hallmark of severe HIVE. The cellular localization of NEBR1 signal is concentrated in the multinucleated giant cells of HIVE tissue (panel 8D), which dramatically contrasts with the complete lack of NEBR1 signal in the control case (panel 8C). The NEBR1 positive cells also correlate with p24 positive cells as shown in panel 8F), which are not seen in the control tissue (panel 8E).

HAD is the result of a series of pathogenic insults that culminate in synaptic and neuronal death within brain regions involved in cognition and memory. The mechanisms underlying the functional changes observed in neurons during disease remain unknown. Nonetheless, neural injury correlates with immune activation of brain MPs (infiltrating and resident). By using the mRNA differential display technique, we were able to isolate a human gene, NEBR1, which is differentially up-regulated as a result of HIV-infection in human MDM.

Figure 9:
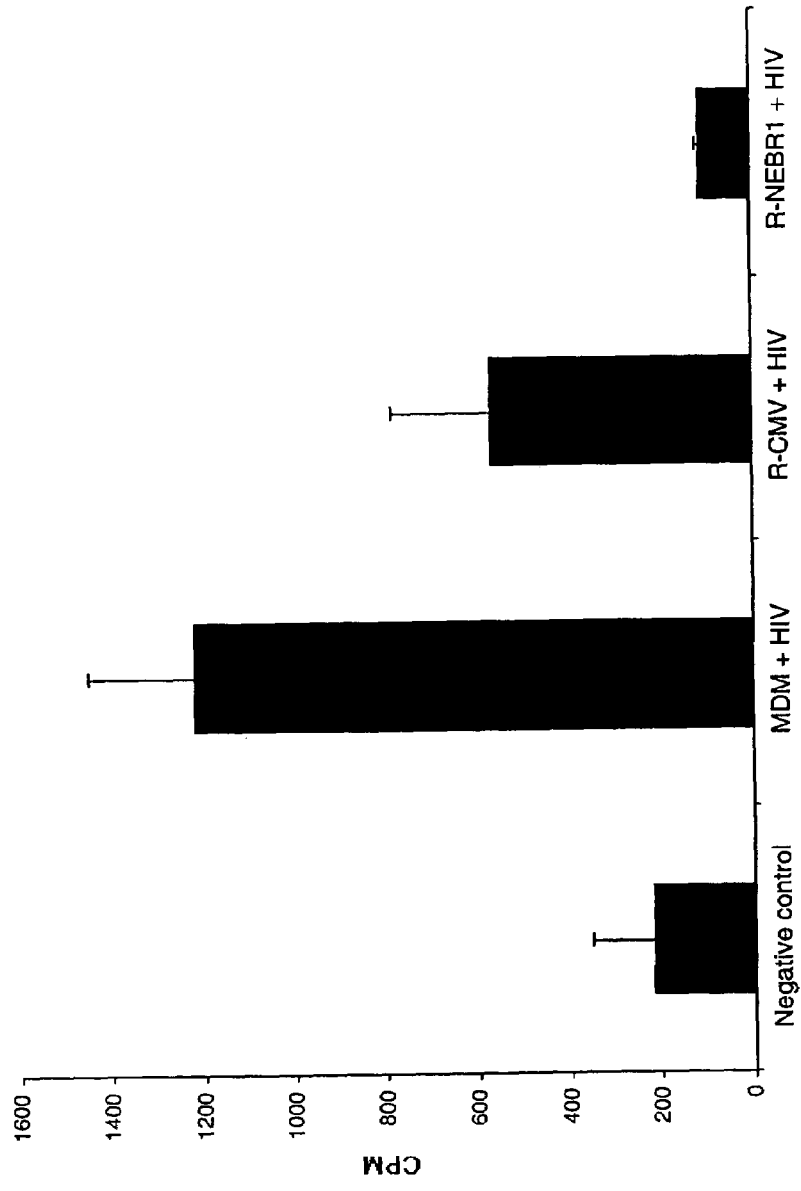
FIG. 9 is a graphs showing the results of a reverse Transcriptase Assay of Human MDMs Infected with Adenoviral Constructs and HIV-1.RT assay was performed as described previously (Vincenzi et al. J. Virol. 73:7515–23, 1999). Human monocytes were cultured for seven days before infection with adenoviral constructs (R-CMV or R-NEBR1) or left untreated as controls. After 24 hours, the adenoviral infection was washed off and the cells were infected with HIV-1 at a multiplicity of infection of 0.1. Supernatant samples were taken at 2, 3 and 4 days post-HIV-1-infection. Representative data from RT assay from day 4 post-HIV-1-infection. The negative control is uninfected media, which demonstrates only background counts. The graph depicts suppression of RT activity with dually infected cells (R-CMV+HIV and R-NEBR1+HIV), but this suppression is more pronounced in the R-NEBR1+HIV MDM.

To confirm these findings, a series of RT-PCR analyses on human MDMs from seven different donors was performed. These cells were either infected with HIV-1 and +/− LPS-activation or not treated (controls). In five out of the seven cases, NEBR1 expression was up-regulated in HIV-1-infected MDM as compared to uninfected or inactivated MDM. See FIG. 9. Therefore demonstrating donor variability in expression of this gene. Upon performing a Chi square analysis for independence (chi square=0.047619048; P-value=0.59338371), we found that the phenotypic pattern of NEBR1 expression conformed to a 3:1 pattern of inheritance. Thus suggesting that up-regulation of NEBR1 could occur as a dominant trait, whereas no increase in expression or down-regulation of this gene could be due to a recessive genotype. If this is true, then this gene may be used as a marker for disease susceptibility. In order to confirm this hypothesis, donor specific genotyping and polymorphism studies will be initiated. Interestingly, from the in vitro studies, we found that LPS-activation had little affect on NEBR1 expression (only 2 in 7 donors). Also, when HIV-1-infection and LPS-activation were used in concert, only two out of seven donors had a significant increase in NEBR1 expression as compared to control MDM and only one donor out of seven showed an increase in NEBR1 expression in HIV-infected/LPS-activated compared to HIV-1-infection alone. This suggests that HIV-infection and LPS-activation could act through different signaling pathways to immune-activate human MPs. In previously published in vitro experiments, primary macrophages have been shown to be protected from HIV-1-infection by treatment of LPS (14, 3, 25, 9,). Our results support this finding, especially in the case of results obtained in HIV-1-infected/LPS-activated MDM compared to control MDMs.

Increased levels of NEBR1 expression in HIVE and HIV positive brain tissues were observed following RT-PCR analyses when compared to the same region of control brain tissues. To further characterize NEBR1, we performed Northern blot analyses on commercially prepared mRNA membranes to determine tissue distribution. Our results demonstrate a ubiquitous distribution of NEBR1 expression in whole tissue with the exception of peripheral blood leukocytes (PBLs), which demonstrated comparatively low levels of basal gene expression. This result is not completely unexpected considering this gene was isolated from cells originating from a monocytic lineage and a not lymphocytic lineage. Because we are interested in differential expression in neurologically damaged brain tissue and cells, we also chose to determine the specific pattern of gene expression in this organ. By quantifying NEBR1 signal from specific brain regions, we found that the cerebellum contains a high basal level of gene expression compared to the other brain regions. This finding is interesting considering NEBR1 was isolated from human MDMs and there is little perivascular infiltration of this cell type into the cerebellum as a result of HIVE resulting from chronic HIV-infection. This finding demonstrates that NEBR1 may have a function outside of disease progression and possibly plays a role in normal development, as suggested by its rather high basal level of expression.

NEBR1, previously randomly cloned and referred to as OTK18 or ZNF175, was initially described as a transcription factor due to the presence of the 13 $C_2H_2$ type zinc fingers contained within its sequence (18). Zinc-finger proteins are a group of eukaryotic genes, which function as transcription-regulating proteins. Whether these genes act as transcriptional activators or suppressors depends upon the highly evolutionarily conserved structural motifs formed by the interaction of two pairs of cysteines and histidines with a zinc ion. It is this specific sequence motif which determines the specific binding of the zinc-finger protein to the nucleic acid (7, 13,). The zinc-finger consensus sequence of NEBR1 is essentially $CXECGKAFXQKSXLX_2HQRXH$. These sequences are connected to each other by the TGEKPYX consensus sequence. Comparison of the NEBR1 zinc-finger sequences with human ZNF41 and Drosophila Krüppel gene revealed that the Krüppel-type motif was conserved in NEBR1 (18). The results presented herein describe the first functional characterization of NEBR1. By preparing GAL4 binding constructs in conjunction with the Dual Luciferase assays, we found that NEBR1 acts as a transcriptional suppressor. Mutational analyses revealed that NEBR1 suppressor activity lies within amino acids 58–115. Upon further analysis, we found that this domain shares homology with a family of zinc-finger proteins containing the Krüppel-associated box (KRAB) motif, which is a transcription repression domain that is encoded by many transcription factors. Of the several hundred (500–700) human genes which contain the Krüppel-type zinc finger, at least one third of them contain a KRAB motif with domains A and/or B at the amino terminus of the protein (2, 23, 24). On chromosome 19p13, there are greater than 40 KRAB containing zinc-finger proteins and on chromosome 19p13, which is where NEBR1 is located, contains more than 10 of these gene clustered together (2, 20). Mutational analysis of the KRAB domain revealed that both KRAB Box A and an as of yet unknown sequence within NEBR1 were responsible for the suppressive nature of NEBR1. In toto, these results demonstrate that NEBR1 is a novel transcription suppressor of the Krüppel-type containing its suppressive activity in its Box A domain and another sequence in NEBR1.

In order to begin to decipher the cytokines, chemokines, receptor and related genes that are differentially expressed due to increased levels of NEBR1 expression, we chose to perform cDNA array analyses. These arrays demonstrated that a large number of cell surface proteins and chemokine receptors were down-regulated as a result of NEBR1 over-expression. Of these proteins and receptors, the following are most intriguing: CD4 (~11 fold suppression), CXCR-4 (~9 fold suppression) and CCR-5 (~3 fold suppression). In vivo, HIV replication primarily occurs in $CD4^+$ T lymphocytes and MPs (8). The MDM are also capable of being infected in vitro as was shown in this study. Binding of HIV-1 to CD4 is necessary, but not sufficient, for productive infection. In order for productive infection to occur, HIV-1 has to bind to a co-receptor (chemokine receptors CXCR4 or CCR5). These G-protein-coupled receptors usually determine the tropism of the HIV-1 strain. In the case of T-cell tropic virus, the CXCR4 receptor is mainly utilized and in the case of macrophage tropic (M-tropic) virus, the CCR5 receptor is utilized (5). But, there are cases of dual-tropism where both CXCR4 and CCR5 receptors are used. In the case of M-tropic HIV, levels of CCR5 receptor on macrophages may determine their susceptibility to infection by HIV-1 (16). But, these cells also readily express detectable concentrations of CXCR4 receptor and it is only is latent steps of the replication cycle of HIV that they encounter some type of block (19). Also, granular staining of CXCR4 is found in multinucleated giant cells of HIV-infected brains (15). Taken together, these data suggest that a decrease in levels of expression of any of these receptors (CD4, CCR5 or CXCR4) may lead to decrease entry and infectivity of HIV-1 to MDMs. Our results indicate that over-expression of NEBR1 can lead to the down-regulation of these receptors.

To support the hypothesis that NEBR1 can regulate HIV-1 infectivity of MDM, we performed RT assays of viral kinetics on different days post-infection of HIV-1 to cells that had previously been infected with adenoviral constructs containing full length NEBR1. The data suggest that NEBR1 acts to inhibit either viral entry or viral replication in MDM. Luciferase binding assays demonstrated that NEBR1 binds to HIV-LTR to suppress basal and HIV-Tat induced HIV-RNA transcription. KRAB containing tetracycline binding protein has been shown to suppress HIV genomic replication through randomly integrated tetracycline response element within the HIV genomic sequence (Herchenroder, O., et al., Biochim Biophys Acta 1445: 216–223, 1999), thereby demonstrating that HIV genomic replication can be suppressed by KRAB containing transcriptional factor upon binding to any of HIV genomic sequence. Ray et al. reported that MBP-1 (c-myc promoter binding protein) inhibits HIV-LTR transcriptional activity and HIV-1 replication by its overexpression (Ray R. B., et al, J. Cell Biochem 64: 565–572, 1997). However MBP-1 has not been characterized in HIV-1 infected leucocytes nor is it a family member of the zinc finger proteins or KRAB containing proteins.

Figure 10:
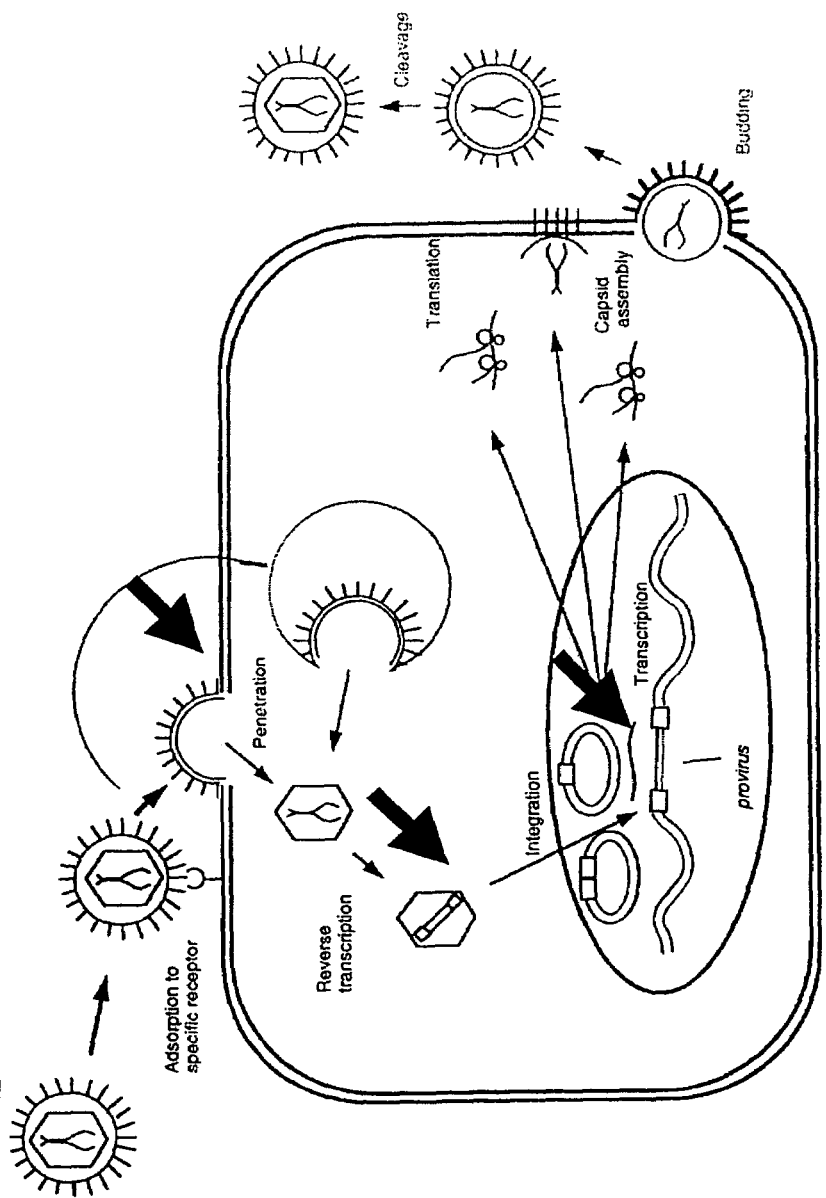
FIG. 10 is a schematic diagram showing the putative multistep viral inhibition mechanism proposed for NEBR1. The arrows indicated the viral replication steps where NEBR1 exerts its potential inhibitory effects.

Our results reveal that NEBR1 is the first endogenous transcriptional factor naturally upregulated in HIV-1 infected cells which antagonizes HIV-1 amplification in multiple steps. A schematic diagram showing the step whereby NEBR1 may exert its anti-viral activity is provided in FIG. 10.

Immunohistochemical analyses demonstrated a dramatic increase in NEBR1 signal in CD68+/p24+ multinucleated giant cells in HIVE brain tissue. Moreover, the NEBR1 signal was completely absent in HIV-1 seronegative tissue, even when CD68+ cells were present. This suggests that NEBR1 is specifically expressed in disease tissue, possibly as a defense mechanism to HIV-1 infection. The complete absence of NEBR1 signal in control tissue, as compared to the specific positive signal seen in HIVE tissue, indicates that detection of NEBR1 expression is of of diagnostic importance.

In summary, we have characterized a novel transcription suppressor from HIV-1-infected MDM, which we refer to as NEBR1. This gene is up-regulated both in vivo and in vitro, as well as being ubiquitously expressed in whole tissue. The over-expression of this gene downregulates specific chemokine receptor expression which is responsible for HIV-1 entry into the MDM. It also demonstrates the ability to decrease infectivity of MDM by HIV-1 as seen by RT analyses and Luciferase Binding assays. Most importantly, immunohistochemical analyses demonstrate that NEBR1 serves as a new diagnostic marker for HAD.

EXAMPLE II

Methods for the Inhibition of HIV-1 Replication in Host Cells

The identification of NEBR1 a target for upregulation in HIV infected macrophages provides the basis for methods to inhibit HIV replication in targeted host cells. Therapeutic approaches for the treatment of HIV-1 infected patients, including acquired immune deficiency syndrome (AIDS), entail viral mediated delivery of full length and truncated NEBR1 genes in combination with antiretroviral therapies. Such therapies, include, without limitation, reverse transcriptase (RT) inhibitors, non-nucleoside inhibitors, and HIV-protease inhibitors. Exemplary viral gene transfer systems include adenovirus, adeno-associated virus, herpesvirus, cytomegarovirus, retrovirus, and lentivirus. The gene transfersystems also include liposome, polyethylene glycol, and gold particle (known as Gene Gun) systems. Methods for the administration of the above-identified anti-viral agents are readily available to the skilled clinician.

Methods for diagnostic assessment of HIV-1 mediated inflammatory reaction including encephalitis are also provided herein. NEBR1-specific polyclonal/monoclonal antibody may be used to advantage in diagnostic assays to assess specific cellular responses to anti-viral and adjuvant therapies.

REFERENCES

1. Akiyama, H. (1994). Inflammatory response in Alzheimer's disease. Tohoku J Exp Med 174, 295–303.
2. Bellefroid, E. J., Poncelet, D. A., Lecocq, P. J., Revelant, O., and Martial, J. A. (1991). The evolutionarily conserved Kruppel-associated box domain defines a subfamily of eukaryotic multifingered proteins. Proc Natl Acad Sci USA 88, 3608–12.
3. Bernstein, M. S., Tong-Starksen, S. E., and Locksley, R. M. (1991). Activation of human monocyte—derived macrophages with lipopolysaccharide decreases human immunodeficiency virus replication in vitro at the level of gene expression. J Clin Invest 88, 540–5.
4. Chen, S., Frederickson, R. C., and Brunden, K. R. (1996). Neuroglial-mediated immunoinflammatory responses in Alzheimer's disease; complement activation and therapeutic approaches. Neurobiol Aging 17, 781–7.
5. Cocchi, F., DeVico, A. L., Garzino-Demo, A., Arya, S. K., Gallo, R. C., and Lusso, P. (1995). Identification of RANTES, MIP-1 alpha, and MIP-1 beta as the major HIV-supressive factors produced by CD8+ T cells [see comments]. Science 270, 1811–5.

6. Elmquist, J. K., Scammell, T. E., and Saper, C. B. (1997). Mechanisms of CNS response to systemic immune challenge: the febrile response. Trends Neurosci 20, 565–70.
7. Evans, R. M., and Hollenberg, S. M. 1998). Zinc fingers: gilt by association [published erratum appears in Cell 1988 Mar. 11; 52(5): 783]. Cell 52, 1–3.
8. Fauci, A. S. (1996). Host factors and the pathogenesis of HIV-induced disease. Nature 384, 529–34.
9. Franchin, G., Zybarth, G., Dai, W. W., Dubrovsky, L., Reiling, N., Schmidtmayerova, H., Bukrinsky, M., and Sherry, B. (2000). Lipopolysaccharide inhibits HIV-1 infection of monocyte-derived macrophages through direct and sustained down-regulation of CC chemokine receptor 5. J Immunol 164, 2592–601.
10. Haga, S., Akai, K., and Ishii, T. (1989). Demonstration of microglial cells in and around senile (neuritic) plaques in the Alzheimer brain. An immunohistochemical study using a novel monoclonal antibody. Acta Neuropathol 77, 569–75.
11. Huitinga, I., van Rooijen, N., de Groot, C. J., Uitdehaag, B. M., and Dijkstra, C. D. (1990). Suppression of experimental allergic encephalomyelitis in Lewis rats after elimination of macrophages. J Exp Med 172, 1025–33.
12. Imamoto, K., and Leblond, C. P. (1977). Presence of labeled monocytes, macrophages and microglia in a stab wound of the brain following an injection of bone marrow cells labeled with 3H-uridine into rats. J Comp Neurol 174, 255–79.
13. Kadonaga, J. T., Carner, K. R., Masiarz, F. R., and Tjian, R. (1987). Isolation of cDNA encoding transcription factor Sp1 and functional analysis of the DNA binding domain. Cell 51, 1079–90.
14. Kornbluth, R. S., Oh, P. S., Munis, J. R., Cleveland, P. H., and Richman, D. D. (1989). Interferons and bacterial lipopolysaccharide protect macrophages from productive infection by human immunodeficiency virus in vitro. J Exp Med 169, 1137–51.
15. Lavi, E., Strizki, J. M., Ulrich, A. M., Zhang, W., Fu, L., Wang, Q., O'Connor, M., Hoxie, J. A., and Gonzalez-Scarano, F. (1997). CXCR-4 (Fusin), a co-receptor for the type 1 human immunodeficiency virus (HIV-1), is expressed in the human brain in a variety of cell types, including microglia and neurons. Am J Pathol 151, 1035–42.
16. Martin, J. C., and Bandres, J. C. (1999). Cells of the monocyte-macrophage lineage and pathogenesis of HIV-1 infection. J Acquir Immune Defic Syndr 22, 413–29.
17. Marty, S., Dusart, I., and Peschanski, M. (1991). Glial changes following an excitotoxic lesion in the CNS--I. Microglia/macrophages. Neuroscience 45, 529–39.
18. Saito, H., Fujiwara, T., Takahashi, E. I., Shin, S., Okui, K., and Nakamura, Y. (1996). Isolation and mapping of a novel human gene encoding a protein containing zinc-finger structures. Genomics 31, 376–9.
19. Schmidtmayerova, H., Alfano, M., Nuovo, G., and Bukrinsky, M. (1998). Human immunodeficiency virus type 1 T-lymphotropic strains enter macrophages via a CD4– and CXCR4-mediated pathway: replication is restricted at a postentry level. J Virol 72, 4633–42.
20. Shannon, M., Ashworth, L. K., Mucenski, M. L., Lamerdin, J. E., Branscomb, E., and Stubbs, L. (1996). Comparative analysis of a conserved zinc finger gene cluster on human chromosome 19q and mouse chromosome 7. Genomics 33, 112–20.
21. Sutcliffe, J. G. (1988). mRNA in the mammalian central nervous system. Annu Rev Neurosci 11, 157–98.
22. Tan, J., Town, T., Paris, D., Mori, T., Suo, Z., Crawford, F., Mattson, M. P., Flavell, R. A., and Mullan, M. (1999). Microglial activation resulting from CD40–CDL40L interaction after beta-amyloid stimulation. Science 286, 2352–5.
23. Thiesen, H. J., and Meyer, W. (1993). Krab domains analyzed in human Cys/His-type zinc-finger proteins KOX 1, KOX 8, and KOX 19. Ann N Y Acad Sci 684, 243–5.
24. Witzgall, R., O'Leary, E., Leaf, A., Onaldi, D., and Bonventre, J. V. (1994). The Kruppel-associated box-A (KRAB-A) domain of zinc finger proteins mediates transcriptional repression. Proc Natl Acad Sci USA 91, 4514–8.
25. Zybarth, G., Reiling, N., Schmidtmayerova, H., Sherry, B., and Bukrinsky, M. (1999). Activation-induced resistance of human macrophages to HIV-1 infection in vitro. J Immunol 162, 400–6.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An antibody immunologically specific for a fragment of NEBR1 selected from the group consisting of amino acids 1–115, 1–241, 1–300, and 58–115 of SEQ ID NO: 2.

2. An antibody as claimed in claim 1, wherein said antibody is polyclonal.

3. An antibody as claimed in claim 1, wherein said antibody is monoclonal.

4. A method for identifying NEBR1 expression in a biological sample, comprising contacting said sample with an antibody as claimed in claim 1, wherein said antibody is detectably labeled and determining the presence of NEBR1 expression as a function of the amount of detectably labeled antibody bound by the sample relative to control cells.

5. A method as claimed in claim 4, wherein said detectable label is selected from the group consisting of fluorescein, texas red and rhodamine.

6. A method as claimed in claim 4, wherein said biological sample is selected from the group consisting of brain tissue, polymorphonuclear blood mononucleocytes, macrophages and CD4+ T cells.

7. A method for identifying NEBR1 expression in a biological sample, comprising contacting said sample with a detectably labeled antibody immunologically specific for NEBR1 and determining the presence of NEBR1 expression as a function of the amount of detectably labeled antibody bound by the sample relative to control cells, wherein said biological sample comprises HIV-1 infected cells.

8. A method as claimed in claim 7, wherein said detectable label is selected from the group consisting of fluorescein, texas red and rhodamine.

9. A method as claimed in claim 7, wherein said HIV-infected cells are selected from the group consisting of brain cells, polymorphonuclear blood mononucleocytes.

* * * * *

SEQUENCE LISTING

<160> NUMBER OF SEQ ID NOS: 14

<210> SEQ ID NO 1
<211> LENGTH: 3734
<212> TYPE: DNA
<213> ORGANISM: Homo sapiens

<400> SEQUENCE: 1

```
gctaagccta tgtcgcttac tggacgctga agtgattggg aatattagca gtgggggttc      60
tgtagggtca ggaaggggcg gctggctttg ggggagtgat gagggcttg ttgggggtgg      120 gggtgcgtga taaagggatt tctcggctga agacgaggct gtgaggcttc tgcagaaccc     180
ccaggtcagg ccacatcatt gaggctgcag gatctctctt catagcccag tacgactctc     240
```

-continued

```
cgccgtgtcc ctggttggaa atccaaaca cctatccagc ttctggctcc tgggaaaagt      300
ggagttgtca gcaagagaga ccgagagtag aagcccagag tggagatgcc tgctgatgtg      360
aatttatccc agaagcctca ggtcctgggt ccagagaagc aggatggatc ttgcgaggca      420
tcagtgtcat ttgaggacgt gaccgtggac ttcagcaggg aggagtggca gcaactggac      480
cctgcccaga gatgcctgta ccgggatgtg atgctggagc tctatagcca tctcttcgca      540
gtggggtatc acattcccaa cccagaggtc atcttcaaga tgctaaaaga aaaggagccg      600
cgtgtggagg aggctgaagt ctcacatcag aggtgtcaag aaagggagtt tgggcttgaa      660
atcccacaaa aggagatttc taagaaagct tcatttcaaa aggatatggt aggtgagttc      720
acaagagatg gttcatggtg ttccatttta gaagaactga ggctggatgc tgaccgcaca      780
aagaaagatg agcaaaatca aattcaaccc atgagtcaca gtgctttctt caacaagaaa      840
acattgaaca cagaaagcaa ttgtgaatat aaggaccctg ggaaaatgat tcgcacgagg      900
ccccaccttg cttcttcaca gaaacaacct cagaaatgtt gcttatttac agaaagtttg      960
aagctgaacc tagaagtgaa cggtcagaat gaaagcaatg acacagaaca gcttgatgac     1020
gttgttgggt ctggtcagct attcagccat agctcttctg atgcctgcag caagaatatt     1080
catacaggag agacattttg caaaggtaac cagtgtagaa aagtctgtgg ccataaacag     1140
tcactcaagc aacatcaaat tcatactcag aagaaaccag atggatgttc tgaatgtggg     1200
gggagcttca cccagaagtc acacctcttt gcccaacaga gaattcatag tgtaggaaac     1260
ctccatgaat gtggcaaatg tggaaaagcc ttcatgccac aactaaaact cagtgtatat     1320
ctgacagatc atacaggtga tataccctgt atatgcaagg aatgtgggaa ggtctttatt     1380
cagagatcag aattgcttac gcaccagaaa acacacacta gaaagaagcc ctataaatgc     1440
catgactgtg gaaaagcctt tttccagatg ttatctctct tcagacatca gagaactcac     1500
agtagagaaa aactctatga atgcagtgaa tgtggcaaag gcttctccca aaactcaacc     1560
ctcattatac atcagaaaat tcatactggt gagagacagt atgcatgcag tgaatgtggg     1620 aaagcctta cccagaagtc aacactcagc ttgcaccaga gaatccactc agggcagaag     1680
tcctatgtgt gtatcgaatg cgggcaggcc ttcatccaga aggcacacct gattgtccat     1740
caaagaagcc acacaggaga aaaaccttat cagtgccaca actgtgggaa atccttcatt     1800
tccaagtcac agcttgatat acatcatcga attcatacag gggagaaacc ttatgaatgc     1860
agtgactgtg gaaaaacctt cacccaaaag tcacacctga atatacacca gaaaattcat     1920 actgagaaa gacaccatgt atgcagtgaa tgcgggaaag ccttcaacca gaagtcaata     1980
ctcagcatgc atcagagaat tcacaccgga gagaagcctt acaaatgcag tgaatgtggg     2040
aaagccttca cttctaagtc tcaattcaaa gagcatcagc gaattcacac gggtgagaaa     2100
ccctatgtgt gcactgaatg tgggaaggcc ttcaacggca ggtcaaattt ccataaacat     2160
caaataactc acactagaga gaggcctttt gtctgttaca atgtgggaa ggcttttgtc      2220 cagaaatcag agttgattac ccatcaaaga actcacatgg agagaaacc ctatgaatgc      2280 cttgactgtg ggaaatcgtt cagtaagaaa ccacaactca ggtgcatca gcgaattcac      2340 acgggagaaa gaccttatgt gtgttctgaa tgtggaaagg ccttcaacaa caggtcaaac     2400
ttcaataaac accaaacaac tcataccaga gacaaatctt acaaatgcag ttattctgtg     2460 aaaggctta ccaagcaatg aattcctagt gcatcagcat attcataaat gaaatatact      2520
ccgagtttct tgaagaagag aacatcttct cagaatcagg tctaattata tgttattgaa     2580
ttcatgcttc agaaaaactc tagggatgca ctgcatgtgt gaacacatga taaaaaagtc     2640
```

-continued

```
atgctttatt ttagtgaggg caattacaga gaaaagagta agcagaaatg tccttctgag    2700
tactggcctc attaaggatt ataaatttc tccccgggaa gaaaccctga ctaacgcatt     2760
gagaaaagcc tttctgtaaa gaatggtaca agacaggttg ttactcgatt atttatagta   2820
aaatatgtgg gaattatat caatgataac cctgtttatt gtgggatatc aatatttta     2880 aagtgccaac acagtcatga taggacaata ttttatgtgt gtgtgtgcgc cttatgtata   2940
taagcatata tataatatat aagcatatta ttatatacag gttgagtatc ccttctccaa   3000
aatgcctggg atcagaagca ttttggattt cagatactta cagattttgg aatatttgca   3060
ttatatttat tggttgagca tccctaatct gaaaatccaa gattaaatgc tccaattagc   3120
atttcctttg agcgtcatgt tagagttcaa aaagtttcag attttgggtt ttcagattag   3180
gaatacccaa cctgtatgta cgtatatttc tgtatctatg tatgtatata tatgcatatg   3240
cagacatatg tatatggtct ggtcagcata tgtgtatgta tgcgtatgta tgtatgtatg   3300
tatgccctca gtgcagtggg gtttgctgca gaattcactg catagcagga gatgtaagca   3360
gatgagttat ttttaagag aatctaatct aattgttttt ataaaaatta ttccctattg   3420
aatatttata taatgaggtt gtatcaacaa tgattaactc ctttattata catacacatg   3480
aatgtgcatt tttggtaaat gcataaatga gattctataa tgtttactga tctttatatt   3540
acagattttc tcttctttta ggattagctc agcttgcccc cccttccat ctccaccatc    3600 tatagtgagc ctctccataa ttagtgccaa ccattagtct cgttcatatt tttacaccag   3660
gagtcaacaa actgtgccat tggccaaata tggcctccca actgtttttt taaaataaag   3720
ttttattgga acac                                                     3734
```

<210> SEQ ID NO 2
<211> LENGTH: 711
<212> TYPE: PRT
<213> ORGANISM: Homo sapiens

<400> SEQUENCE: 2

```
Met Pro Ala Asp Val Asn Leu Ser Gln Lys Pro Gln Val Leu Gly Pro
 1               5                  10                  15

Glu Lys Gln Asp Gly Ser Cys Glu Ala Ser Val Ser Phe Glu Asp Val
            20                  25                  30

Thr Val Asp Phe Ser Arg Glu Glu Trp Gln Gln Leu Asp Pro Ala Gln
        35                  40                  45

Arg Cys Leu Tyr Arg Asp Val Met Leu Glu Leu Tyr Ser His Leu Phe
    50                  55                  60

Ala Val Gly Tyr His Ile Pro Asn Pro Glu Val Ile Phe Arg Met Leu
65                  70                  75                  80

Lys Glu Lys Glu Pro Arg Val Glu Ala Glu Val Ser His Gln Arg
                85                  90                  95

Cys Gln Glu Arg Glu Phe Gly Leu Glu Ile Pro Gln Lys Glu Ile Ser
            100                 105                 110

Lys Lys Ala Ser Phe Gln Lys Asp Met Val Gly Glu Phe Thr Arg Asp
        115                 120                 125

Gly Ser Trp Cys Ser Ile Leu Glu Glu Leu Arg Leu Asp Ala Asp Arg
    130                 135                 140

Thr Lys Lys Asp Glu Gln Asn Gln Ile Gln Pro Met Ser His Ser Ala
145                 150                 155                 160

Phe Phe Asn Lys Lys Thr Leu Asn Thr Glu Ser Asn Cys Glu Tyr Lys
                165                 170                 175
```

-continued

```
Asp Pro Gly Lys Met Ile Arg Thr Arg Pro His Leu Ala Ser Ser Gln
            180                 185                 190
Lys Gln Pro Gln Lys Cys Cys Leu Phe Thr Glu Ser Leu Lys Leu Asn
        195                 200                 205
Leu Glu Val Asn Gly Gln Asn Glu Ser Asn Asp Thr Glu Gln Leu Asp
    210                 215                 220
Asp Val Val Gly Ser Gly Gln Leu Phe Ser His Ser Ser Asp Ala
225                 230                 235                 240
Cys Ser Lys Asn Ile His Thr Gly Glu Thr Phe Cys Lys Gly Asn Gln
                245                 250                 255
Cys Arg Lys Val Cys Gly His Lys Gln Ser Leu Lys Gln His Gln Ile
            260                 265                 270
His Thr Gln Lys Lys Pro Asp Gly Cys Ser Glu Cys Gly Gly Ser Phe
        275                 280                 285
Thr Gln Lys Ser His Leu Phe Ala Gln Gln Arg Ile His Ser Val Gly
    290                 295                 300
Asn Leu His Glu Cys Gly Lys Cys Gly Lys Ala Phe Met Pro Gln Leu
305                 310                 315                 320
Lys Leu Ser Val Tyr Leu Thr Asp His Thr Gly Asp Ile Pro Cys Ile
                325                 330                 335
Cys Lys Glu Cys Gly Lys Val Phe Ile Gln Arg Ser Glu Leu Leu Thr
            340                 345                 350
His Gln Lys Thr His Thr Arg Lys Lys Pro Tyr Lys Cys His Asp Cys
        355                 360                 365
Gly Lys Ala Phe Phe Gln Met Leu Ser Leu Phe Arg His Gln Arg Thr
    370                 375                 380
His Ser Arg Glu Lys Leu Tyr Glu Cys Ser Glu Cys Gly Lys Gly Phe
385                 390                 395                 400
Ser Gln Asn Ser Thr Leu Ile Ile His Gln Lys Ile His Thr Gly Glu
                405                 410                 415
Arg Gln Tyr Ala Cys Ser Glu Cys Gly Lys Ala Phe Thr Gln Lys Ser
            420                 425                 430
Thr Leu Ser Leu His Gln Arg Ile His Ser Gly Gln Lys Ser Tyr Val
        435                 440                 445
Cys Ile Glu Cys Gly Gln Ala Phe Ile Gln Lys Ala His Leu Ile Val
    450                 455                 460
His Gln Arg Ser His Thr Gly Glu Lys Pro Tyr Gln Cys His Asn Cys
465                 470                 475                 480
Gly Lys Ser Phe Ile Ser Lys Ser Gln Leu Asp Ile His His Arg Ile
                485                 490                 495
His Thr Gly Glu Lys Pro Tyr Glu Cys Ser Asp Cys Gly Lys Thr Phe
            500                 505                 510
Thr Gln Lys Ser His Leu Asn Ile His Gln Lys Ile His Thr Gly Glu
        515                 520                 525
Arg His His Val Cys Ser Glu Cys Gly Lys Ala Phe Asn Gln Lys Ser
    530                 535                 540
Ile Leu Ser Met His Gln Arg Ile His Thr Gly Glu Lys Pro Tyr Lys
545                 550                 555                 560
Cys Ser Glu Cys Gly Lys Ala Phe Thr Ser Lys Ser Gln Phe Lys Glu
                565                 570                 575
His Gln Arg Ile His Thr Gly Glu Lys Pro Tyr Val Cys Thr Glu Cys
            580                 585                 590
```

-continued

Gly Lys Ala Phe Asn Gly Arg Ser Asn Phe His Lys His Gln Ile Thr
            595                 600                 605

His Thr Arg Glu Arg Pro Phe Val Cys Tyr Lys Cys Gly Lys Ala Phe
    610                 615                 620

Val Gln Lys Ser Glu Leu Ile Thr His Gln Arg Thr His Met Gly Glu
625                 630                 635                 640

Lys Pro Tyr Glu Cys Leu Asp Cys Gly Lys Ser Phe Ser Lys Pro
                645                 650                 655

Gln Leu Lys Val His Gln Arg Ile His Thr Gly Glu Arg Pro Tyr Val
            660                 665                 670

Cys Ser Glu Cys Gly Lys Ala Phe Asn Asn Arg Ser Asn Phe Asn Lys
            675                 680                 685

His Gln Thr Thr His Thr Arg Asp Lys Ser Tyr Lys Cys Ser Tyr Ser
    690                 695                 700

Val Lys Gly Phe Thr Lys Gln
705                 710

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
gaaaatccaa acacctatcc                                               20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
aaggacattt ctgcttactc                                               20

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5
ggctgtcttc caataaaac                                                19

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
gtgagcctct ccataattag                                               20

<210> SEQ ID NO 7
<211> LENGTH: 99
<212> TYPE: PRT
<213> ORGANISM: Homo sapiens

```
<400> SEQUENCE: 7

Met Ala Ala Asn Gly Asp Ser Pro Pro Trp Ser Pro Ala Leu Ala Ala
1               5                   10                  15

Glu Gly Arg Gly Ser Ser Cys Glu Ala Ser Val Ser Phe Glu Asp Val
            20                  25                  30

Thr Val Asp Phe Ser Lys Glu Gly Trp Gln His Leu Asp Pro Ala Gln
        35                  40                  45

Arg Arg Leu Tyr Trp Asp Val Thr Leu Glu Asn Tyr Ser His Leu Leu
    50                  55                  60

Ser Val Gly Tyr Gln Ile Pro Lys Ser Glu Ala Ala Phe Lys Leu Glu
65                  70                  75                  80

Gln Gly Glu Gly Pro Trp Met Leu Glu Gly Glu Ala Pro His Gln Ser
                85                  90                  95

Cys Ser Gly

<210> SEQ ID NO 8
<211> LENGTH: 84
<212> TYPE: PRT
<213> ORGANISM: Homo sapiens

<400> SEQUENCE: 8

Met Ala Pro Glu Gln Arg Glu Gly Ala Ser Gln Val Ser Val Thr Phe
1               5                   10                  15

Glu Asp Val Ala Val Leu Phe Thr Arg Asp Glu Trp Lys Lys Leu Asp
            20                  25                  30

Leu Ser Gln Arg Ser Leu Tyr Arg Glu Val Met Leu Glu Asn Tyr Ser
        35                  40                  45

Asn Leu Ala Ser Met Ala Gly Phe Leu Phe Thr Lys Pro Lys Val Ile
    50                  55                  60

Ser Leu Leu Gln Gln Gly Glu Asp Pro Trp Gln Val Glu Lys Glu Gly
65                  70                  75                  80

Pro Arg Tyr Phe

<210> SEQ ID NO 9
<211> LENGTH: 99
<212> TYPE: PRT
<213> ORGANISM: Homo sapiens

<400> SEQUENCE: 9

Met Pro Ala Asn Gly Thr Ser Pro Gln Arg Phe Pro Ala Leu Ile Pro
1               5                   10                  15

Gly Glu Pro Gly Arg Ser Phe Glu Gly Ser Val Ser Phe Glu Asp Val
            20                  25                  30

Ala Val Asp Phe Thr Arg Gln Glu Trp His Arg Leu Asp Pro Ala Gln
        35                  40                  45

Arg Thr Met His Lys Asp Val Met Leu Glu Thr Tyr Ser Asn Leu Ala
    50                  55                  60

Ser Val Gly Leu Cys Val Ala Lys Pro Glu Met Ile Phe Lys Leu Glu
65                  70                  75                  80

Arg Gly Glu Glu Leu Trp Ile Leu Glu Glu Glu Ser Ser Gly His Gly
                85                  90                  95

Tyr Ser Gly
```

```
<210> SEQ ID NO 10
<211> LENGTH: 80
<212> TYPE: PRT
<213> ORGANISM: Homo sapiens

<400> SEQUENCE: 10

Met Asn Lys Ser Leu Gly Pro Val Ser Phe Lys Asp Val Ala Val Asp
1               5                   10                  15

Phe Thr Gln Glu Glu Trp Gln Gln Leu Asp Pro Glu Gln Lys Ile Thr
            20                  25                  30

Tyr Arg Asp Val Met Leu Glu Asn Tyr Ser Asn Leu Val Ser Val Gly
        35                  40                  45

Tyr His Ile Ile Lys Pro Asp Val Ile Ser Lys Leu Glu Gln Gly Glu
    50                  55                  60

Glu Pro Trp Ile Val Glu Gly Glu Phe Leu Leu Gln Ser Tyr Pro Asp
65                  70                  75                  80

<210> SEQ ID NO 11
<211> LENGTH: 79
<212> TYPE: PRT
<213> ORGANISM: Homo sapiens

<400> SEQUENCE: 11

Met Asn Thr Leu Gln Gly Pro Val Ser Phe Lys Asp Val Ala Val Asp
1               5                   10                  15

Phe Thr Gln Glu Glu Trp Gln Gln Leu Asp Pro Asp Glu Lys Ile Thr
            20                  25                  30

Tyr Arg Asp Val Met Leu Glu Asn Tyr Ser His Leu Val Ser Val Gly
        35                  40                  45

Tyr Asp Thr Thr Lys Pro Asn Val Ile Lys Leu Glu Gln Gly Glu
    50                  55                  60

Glu Pro Trp Ile Met Gly Gly Glu Phe Pro Cys Gln His Ser Pro
65                  70                  75

<210> SEQ ID NO 12
<211> LENGTH: 83
<212> TYPE: PRT
<213> ORGANISM: Rattus norvegicus

<400> SEQUENCE: 12

Met Asn Cys His Ser Val Pro Leu Gln Gly Pro Val Ser Phe Lys Asp
1               5                   10                  15

Val Thr Val Asp Phe Thr Gln Glu Glu Trp Gln Arg Leu Asp Pro Ala
            20                  25                  30

Gln Lys Ala Leu Tyr Arg Asp Val Met Leu Glu Asn Tyr Cys His Phe
        35                  40                  45

Ile Ser Val Gly Phe His Ile Thr Lys Pro Asp Met Ile Arg Lys Leu
    50                  55                  60

Glu Gln Gly Glu Glu Leu Trp Thr Glu Arg Met Phe Pro Ser Gln Ser
65                  70                  75                  80

Tyr Leu Glu

<210> SEQ ID NO 13
<211> LENGTH: 21
<212> TYPE: PRT
<213> ORGANISM: Homo sapiens
<220> FEATURE:
<221> NAME/KEY: ZN_FING
<222> LOCATION: (1)...(21)
```

```
<220> FEATURE:
<221> NAME/KEY: misc_feature
<222> LOCATION: (2)...(20)
<223> OTHER INFORMATION: Xaa = any amino acid

<400> SEQUENCE: 13

Cys Xaa Glu Cys Gly Lys Ala Phe Xaa Gln Lys Ser Xaa Leu Xaa Xaa
1               5                   10                  15

His Gln Arg Xaa His
            20

<210> SEQ ID NO 14
<211> LENGTH: 7
<212> TYPE: PRT
<213> ORGANISM: Homo sapiens
<220> FEATURE:
<221> NAME/KEY: ZN_FING
<222> LOCATION: (1)...(7)
<220> FEATURE:
<221> NAME/KEY: misc_feature
<222> LOCATION: (7)...(7)
<223> OTHER INFORMATION: Xaa = any amino acid

<400> SEQUENCE: 14

Thr Gly Glu Lys Pro Tyr Xaa
1               5
```